United States Patent [19]
Okuma et al.

[11] Patent Number: 6,132,640
[45] Date of Patent: Oct. 17, 2000

[54] QUINOLINE DERIVATIVE AND USE OF SAME

[75] Inventors: Tadashi Okuma; Hideki Ikuta; Tatsuya Nagayoshi; Akira Ogiso; Hisato Ito, all of Fukuoka-ken, Japan

[73] Assignee: Mitsui Chemicals, Inc., Japan

[21] Appl. No.: 08/877,913

[22] Filed: Jun. 18, 1997

[30] Foreign Application Priority Data

| Jun. 28, 1996 | [JP] | Japan | 8-168860 |
|---|---|---|---|
| Jun. 28, 1996 | [JP] | Japan | 8-168861 |
| Oct. 9, 1996 | [JP] | Japan | 8-268592 |
| Dec. 5, 1996 | [JP] | Japan | 8-325402 |
| Dec. 12, 1996 | [JP] | Japan | 8-332135 |

[51] Int. Cl.$^7$ ............ C09K 11/06; H05B 33/14; C07D 215/00
[52] U.S. Cl. .............. 252/301.16; 252/301.26; 252/301.31; 546/10; 546/152; 428/690; 428/691; 428/917; 313/504
[58] Field of Search ............ 428/917, 690, 428/691; 546/10, 154, 155, 159, 171, 175, 152; 252/301.22, 301.26, 301.27, 301.31, 301.6 R, 301.16; 313/483, 504

[56] References Cited

U.S. PATENT DOCUMENTS 3,390,149  6/1968  Kranz et al. ............ 546/175

FOREIGN PATENT DOCUMENTS

| 652274 | 5/1995 | European Pat. Off. . |
| 0761772 A1 | 3/1997 | European Pat. Off. . |
| 56-147784 | 11/1981 | Japan . |

OTHER PUBLICATIONS

"Comprehensive Inorganic Chemistry" edited by J.C. Bailar, H.J. Nyholm, A.F. Trotman–Dickenson, Pergamon Press, vol. 3, pp. 249–251, (No Month), 1973.

Database WPI, Week 8152, Derwent Publications Ltd., London, GB; AN 81–95923d XP002047368 & JP 56147784 A (Tokushu Toryo kK) *abstract*.

*Primary Examiner*—Marie Yamnitzky
*Attorney, Agent, or Firm*—Burns, Doane, Swecker, & Mathis, L.L.P.

[57] ABSTRACT

Quinoline compound, zinc halogenide complex and zinc complex suited for use in an electro-luminescence (EL) element, a fluorescent material and an ultraviolet absorption material, and a preparation process for these compounds are described. These compounds and a tautomer of the same have a strong luminescent intensity and are used for an EL material, the compound of zinc halogenide complex and zinc complex and a tautomer of the same has absorption at a wave length of 400 nm or less and is used for an ultraviolet absorption material, and further the quinoline compound and a tautomer has a strong luminescent intensity and is used for a fluorescent material. The zinc halogenide complex and zinc complex can be prepared by related preparation processes directly from a quinoline derivative and a phthalimide derivative, or by way of the quinoline compound which is obtained from these derivatives.

16 Claims, 9 Drawing Sheets

QUINOLINE DERIVATIVE AND USE OF SAME

BACKGROUND OF THE INVENTION

1. Field of the Invention

The present invention relates to a quinoline compound suited for use in a luminous layer of an electro-luminescence element, the electro-luminescence element and a fluorescent material by using said compound, and a preparation process of said compound.

The invention also relates to a zinc halogenide complex suited for use in a luminous layer of an electro-luminescence element or an ultraviolet absorption material, the electro-luminescence element and the ultraviolet absorption material by using said complex, and a preparation process of said complex.

The invention further relates to a zinc complex suited for use in a luminous layer of an electro-luminescence element or an ultraviolet absorption material, the electro-luminescence element and the ultraviolet absorption material by using said complex, and a preparation process of said complex.

2. Related Art of the Invention

In recent years, on fluorescent materials and luminescent materials have been carried out in order to use these materials for electro-luminescence (EL) elements.

A quinoline having the formula (7):

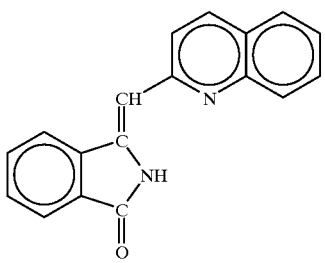

has been known to have fluorescent property as described in Liebigs Ann. Chem., vol.315, p.303(1901) and Chem. Ber., vol.100, p. 2261–2273 (1967).

On the other hand, the EL elements have recently attained a great progress. Luminous layers and positive hole transport layers have been investigated and are approaching practical use [Tsutsui, Saito et. al., Japan Journal of Applied Physics, vol.27, No.2, L269 (1988); vol.27, No.4,L713 (1988)].

Aromatic compounds which exhibit fluorescence in the ultraviolet to visible region have been known [I. B. Berlman, Handbook of Fluorescence Spectra of Aromatic Molecules, published from Academic Press].

Further, inorganic compounds such as titanium dioxide and zinc oxide, and organic compounds such as benzophenone, benzotriazole and other compounds having a triazine structure have been known as ultraviolet absorption materials as disclosed in Japanese Laid-Open Patent Sho 64-20248.

SUMMARY OF THE INVENTION

The first object of the invention is to provide an excellent material as an EL material and a useful preparation process of the material.

The second object of the invention is to provide an excellent material as a fluorescent material and a useful preparation process of the material.

Further, the third object of the invention is to provide an excellent material as an ultraviolet absorption material and a useful preparation process of the material.

These objects can be achieved by the following aspects of the present invention.

(1) A quinoline compound and a tautomer of the same which are represented by the formula (1):

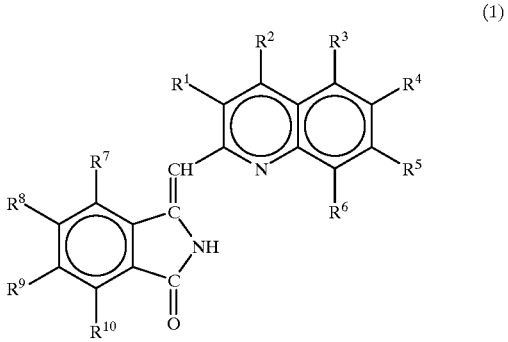

where each of $R^1$, $R^2$, $R^3$, $R^4$, $R^5$, $R^6$, $R^7$, $R^8$, $R^9$ and $R^{10}$ is individually a hydrogen atom, halogen atom, cyano, amino, substituted or unsubstituted alkyl having two or more carbon atoms, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, except the case where all of $R^1$, $R^2$, $R^3$, $R^4$, $R^5$, $R^6$, $R^7$, $R^8$, $R^9$ and $R^{10}$ is a hydrogen atom.

(2) A zinc halogenide complex and a tautomer of the same which are represented by the formula (2):

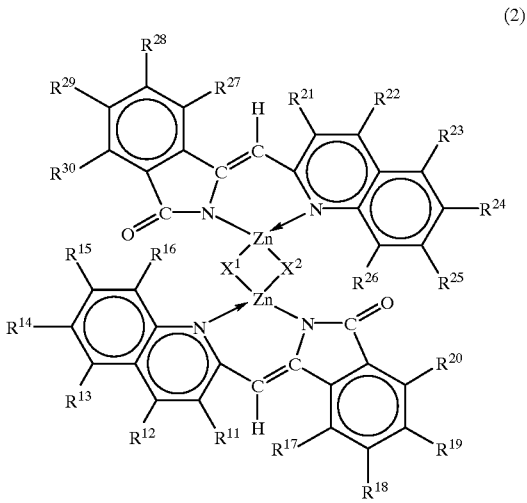

where each of $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$ and $R^{30}$ is individually a hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, and each of $X^1$ and $X^2$ is individually a fluorine, chlorine, bromine or iodine atom.

(3) A zinc complex and tautomer of the same which are represented by the formula (3):

(3)

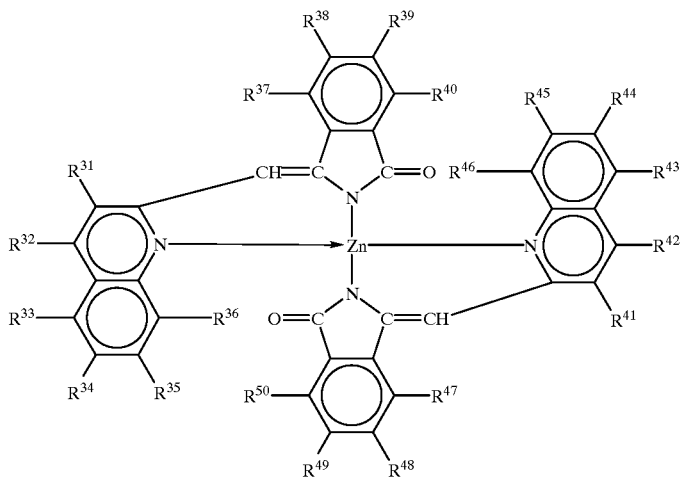

where each of $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$ and $R^{50}$ is individually hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group.

(4) A quinoline compound which has peak intensity at a Bragg angle (2 θ) of 12.8°, 15.2°, 18.3°, 22.5°, 25° and 28.4° on a X-ray diffraction spectrum and is shown by the formula (7):

(7)

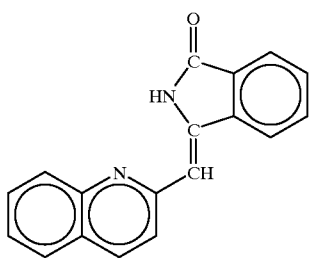

(5) A quinoline compound of the formula (7) wherein the peak intensity ratio of the Bragg angle (2 θ) of 12.8° to the Bragg angle (2 θ) of 15.2° is 0.7 or less.

(6) A preparation process of a quinoline compound and a tautomer of the same which are represented by the formula (4):

(4)

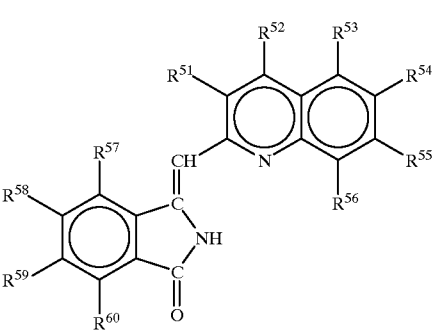

where each of $R^{51}$, $R^{52}$, $R^{53}$, $R^{54}$, $R^{55}$, $R^{56}$, $R^{57}$, $R^{58}$, $R^{59}$, $R^{60}$ is individually hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, comprising reacting a quinoline derivative represented by the formula (5)

(5)

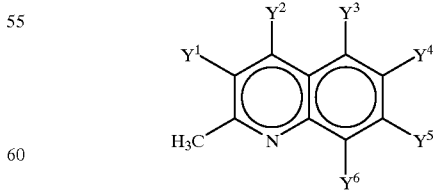

where each of $Y^1$, $Y^2$, $Y^3$, $Y^4$, $Y^5$ and $Y^6$ is a hydrogen atom, halogen atom, nitro, cyano, hydroxy, amino, substituted or unsubstituted alkyl, substituted or unsubstituted aryl, substituted or unsubstituted alkoxy substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, and a phthalimide derivative represented by the formula (6):

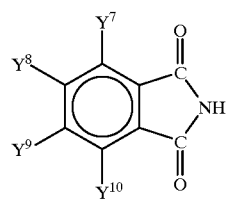

(6)

where each of $Y^7$, $Y^8$, $Y^9$ and $Y^{10}$ is individually a hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, with zinc halogenide in an organic basic solvent and successively treating with an inorganic acid.

(7) A preparation process of a quinoline compound and a tautomer which are represented by the formula (4) wherein a phthalimide derivative represented by the formula (6) is in a molar ratio of 0.5 to 2.0 to a quinoline derivative represented by the formula (5).

(8) A preparation process of a quinoline compound and a tautomer which are represented by the formula (4) wherein a phthalimide derivative represented by the formula (6) is in a molar ratio of 1.1 to 2.0 to a quinoline derivative represented by the formula (5), (9) A preparation process of a quinoline compound represented by the formula (4) and a tautomer of the same comprising treating with an inorganic acid a zinc halogenide complex represented by the formula (2) and a tautomer of the same.

(10) A preparation process of a quinoline compound represented by the formula (4) and a tautomer of the same comprising treating with an inorganic acid a zinc complex represented by the formula (3) and a tautomer of the same.

(11) An electro-luminescence element wherein the luminous layer is a compound represented by the formula (4) and a tautomer of the same.

(12) A fluorescent material comprising a quinoline compound represented by the formula (4) and a tautomer of the same.

(13) A preparation process of a zinc halogenide complex represented by the formula (2) and a tautomer of the same comprising reacting one or two kinds of a quinoline derivative represented by the formula (5) and one or two kinds of a phthalimide derivative represented by the formula (6) with zinc halogenide in an organic solvent.

(14) A preparation process of a zinc halogenide complex represented by the formula (2) and a tautomer of the same comprising reacting a quinoline compound represented by the formula (4) and a tautomer of the same with zinc halogenide in an organic solvent.

(15) An electro-luminescence element wherein the luminous layer is a zinc halogenide complex represented by the formula (2) and a tautomer of the same.

(16) An ultraviolet absorption material comprising a zinc halogenide complex represented by the formula (2) and a tautomer of the same.

(17) A preparation process of a zinc complex represented by the formula (3) and a tautomer of the same comprising heating in organic amine a zinc halogenide complex represented by the formula (2) and a tautomer of the same.

(18) A preparation process of a zinc complex represented by the formula (3) and a tautomer of the same comprising reacting one or two kinds of a quinoline derivative represented by the formula (5) and one or two kinds of a phthalimide derivative represented by the formula (6) with zinc halogenide in an organic solvent.

(19) An electro-luminescence element wherein the luminous layer is a zinc complex represented by the formula (3) and a tautomer of the same.

(20) An ultraviolet absorption material comprising a zinc complex represented by the formula (3) and a tautomer of the same.

The present invention provides the compound represented by the formulas (2), (3) and (4) and a tautomer of the same as an EL material which has a strong luminescent intensity, the compound represented by the formulas (2) and (3) and a tautomer of the same as a specific ultraviolet absorption material which has absorption at a wave length of 400 nm or less, and further the compound represented by the formula (4) and a tautomer of the same as an excellent fluorescent material which has a strong luminescent intensity.

Further, the present invention can prepare these useful materials by related preparation processes directly from the quinoline derivative represented by the formula (5) and the phthalimide derivative represented by the formula (6), or by way of the quinoline compound represented by the formula (4) which is obtained from these derivatives.

That is, the invention provides excellent materials for the EL material, ultraviolet absorption material and fluorescent material, and a useful process of preparing these materials.

BRIEF DESCRIPTION OF THE DRAWINGS

For a more complete understandings of the present invention, reference should be made to the detailed description should be read together with the accompanying drawings, wherein.

DETAILED DESCRIPTION OF THE INVENTION

Figure 1:
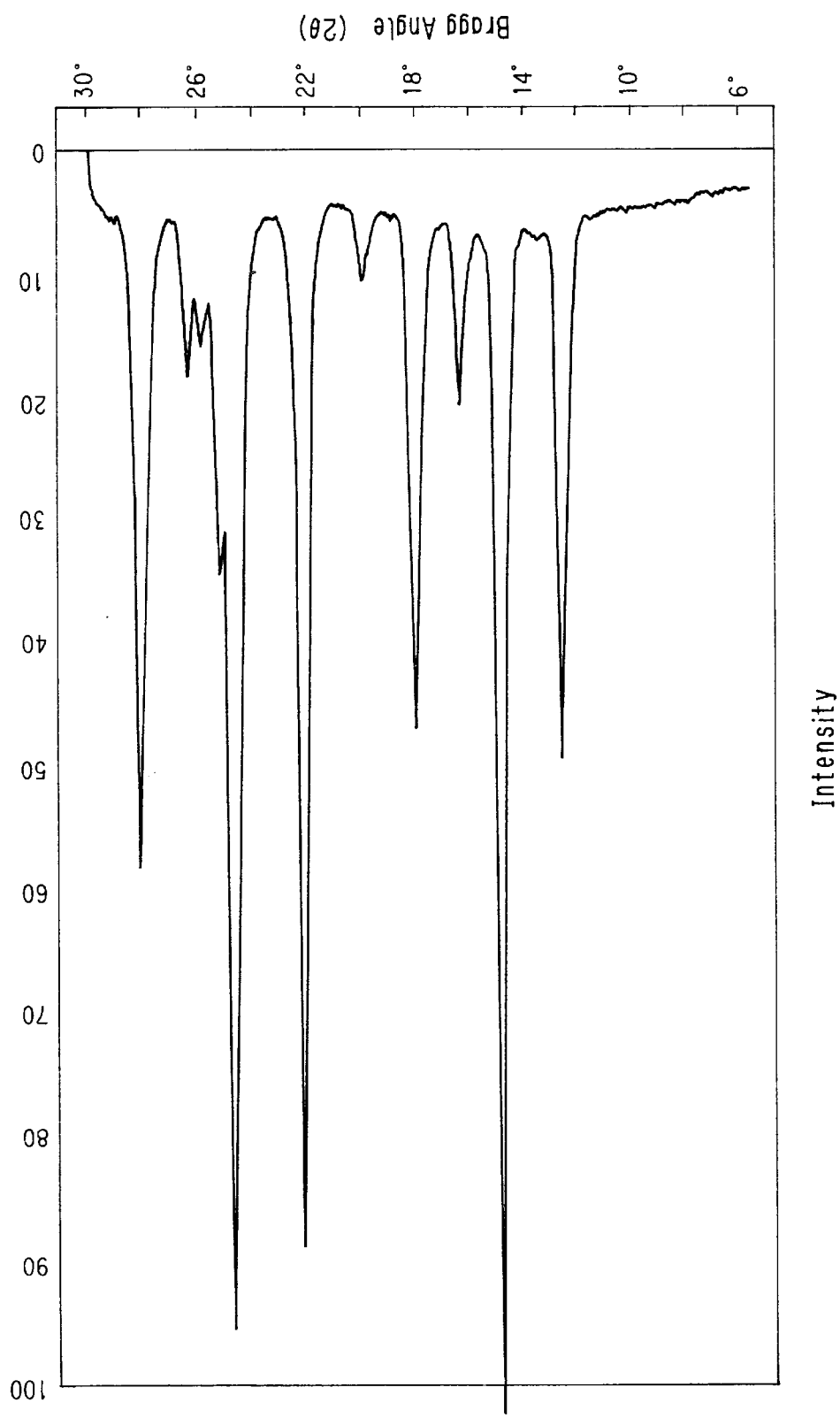
FIG. 1 is a X-ray diffraction spectrum of the quinoline compound obtained in Example 1 and shown by the formula (7).

The present invention will be illustrated in detailed hereinafter.

In the invention, the quinoline compound and the tautomer of the same, and the complex having these compounds as ligands, that is, the zinc halogenide complex and tautomer of the same and the zinc complex and the tautomer of the same can be prepared by way of the process A, process B, process C, process D, process E, process F and process G as illustrated in the reaction step figure.

[Process A] The quinoline compound of the formula (4) and the tautomer of the same can be obtained by reacting the quinoline derivative of the formula (5) and the phthalimide derivative of the formula (6) with zinc halogenide in an organic base solvent and successively treating with an inorganic acid.

[Process B] The quinoline compound of the formula (4) and the tautomer of the same can be obtained by treating the zinc halogenide complex of the formula (2) and the tautomer of the same with an inorganic acid.

[Process C] The quinoline compound of the formula (4) and the tautomer of the same can be obtained by treating the

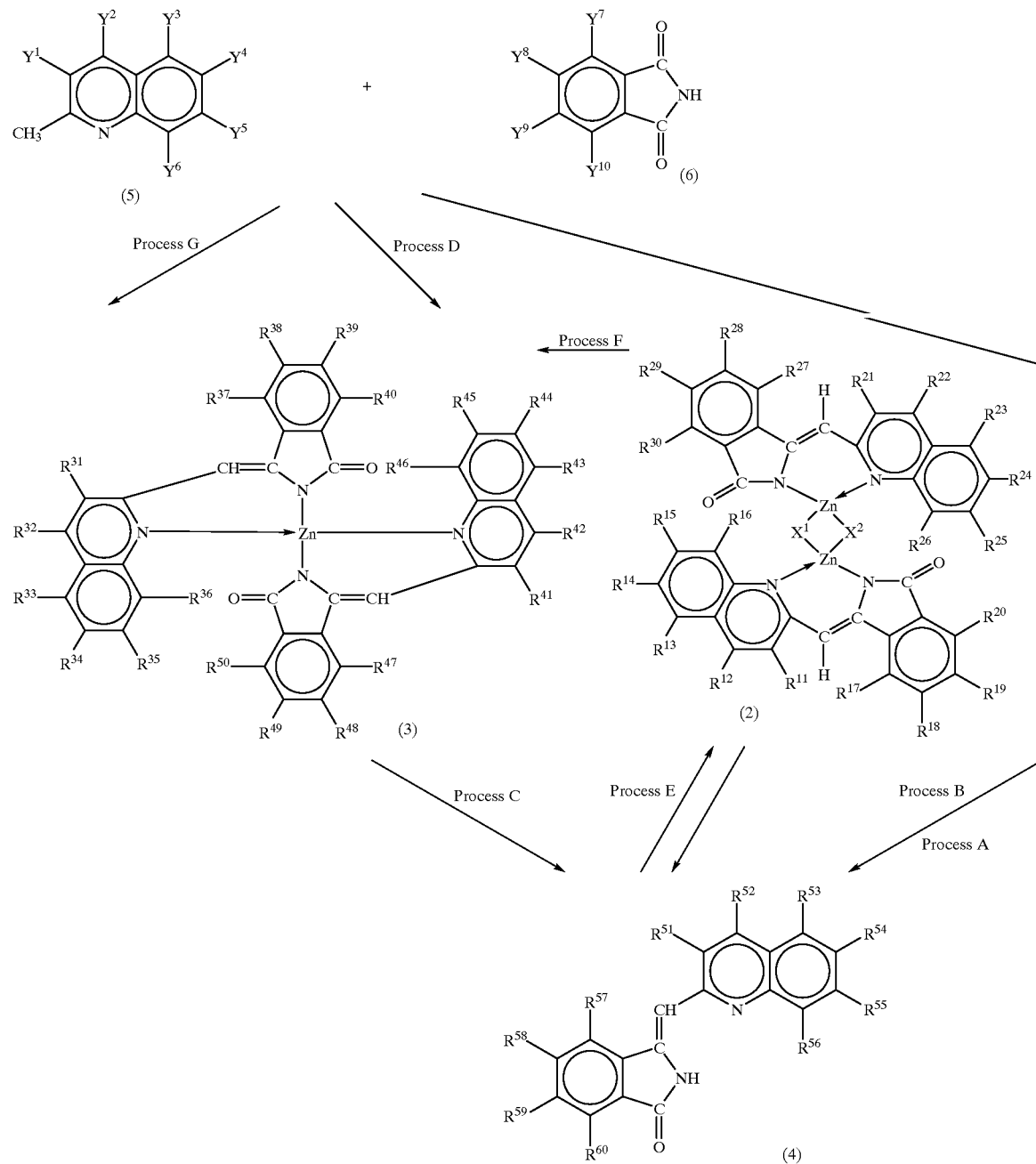

zinc complex of the formula (3) and the tautomer of the same with an inorganic acid.

[Process D] The zinc halogenide complex of the formula (2) and the tautomer of the same can be obtained by reacting one or two kinds of the quinoline derivative of the formula (5) and one or two kinds of the phthalimide derivative of the formula (6) with zinc halogenide in an organic solvent.

[Process E] The zinc halogenide complex of the formula (2) and the tautomer of the same can be obtained by reacting the quinoline compound of the formula (4) and the tautomer of the same with zinc halogenide in an organic solvent.

[Process F] The zinc complex of the formula (3) and the tautomer of the same can be obtained by heating the zinc halogenide complex of the formula (2) and the tautomer of the same in an organic amine.

[Process G] The zinc complex of the formula (3) and the tautomer of the same can be obtained by reacting one or two kinds of the quinoline derivative of the formula (5) and one or two kinds of the phthalimide derivative of the formula (6) with zinc halogenide in an organic solvent.

In Process A, the quinoline compound of the formula (4) can be obtained by successively carrying out Process D and Process B without isolating the zinc halogenide complex of the formula (2).

Alternatively, the quinoline compound of the formula (4) can be obtained by successively carrying out Process D, Process F and Process C without isolating the zinc halogenide complex of the formula (2) and zinc complex of the formula (3).

In the invention, each substituent of the compound (1) is shown by $R^1$, $R^2$, $R^3$, $R^4$, $R^5$, $R^6$, $R^7$, $R^8$, $R^9$ and $R^{10}$, and is individually a hydrogen atom, halogen atom, cyano, amino, substituted or unsubstituted alkyl having two or more carbon atoms, substituted or unsubstituted aryl, substituted or unsubstituted alkoxy, substituted or unsubstituted aryloxy, substituted or unsubstituted N-alkyl amino, substituted or unsubstituted N,N-dialkyl amino, substituted or unsubstituted N-aryl amino, substituted or unsubstituted N,N-diaryl amino or substituted or unsubstituted N-alkyl-N-aryl group.

Each substituent of the compounds (2), (3) and (4) and intermediates thereof, that is, the quinoline derivative (5) and phthalimide derivative (6) is shown by $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $Y^1$, $Y^2$, $Y^3$, $Y^4$, $Y^5$, $Y^6$, $Y^7$, $Y^8$, $Y^9$ and $Y^{10}$; and is individually hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkyl amino, substituted or unsubstituted N,N-dialkyl amino, substituted or unsubstituted N-aryl amino, substituted or unsubstituted N,N-diaryl amino or substituted or unsubstituted N-alkyl-N-aryl amino, and each of $X^1$ and $X^2$ is individually a fluorine, chlorine, bromine or iodine atom.

Practical examples of halogen atoms include a fluorine, chlorine, bromine or iodine atom.

Substituted or unsubstituted alkyl groups which are favorable include, for example, methyl, ethyl, n-propyl radical, iso-propyl, n-butyl, iso-butyl, tert-butyl, sec-butyl, n-pentyl, iso-pentyl, tert-pentyl, sec-pentyl, cyclopentyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,3-dimethylbutyl, 1,1,2-trimethylpropyl, 1,2,2-trimethylpropyl, 1-ethylbutyl, 2-ethylbutyl, 1-ethyl-2-methylpropyl, cyclohexyl, methylcyclopentyl, n-heptyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 1-ethylpentyl, 2-ethylpentyl, 3-ethylpentyl, 1,1,2-trimethylbutyl, 1,1,3-trimethylbutyl, 1,2,3-trimethylbutyl, 1,2,2-trimethylbutyl, 1,3,3-trimethylbutyl, 2,3,3-trimethylbutyl, 1-ethyl-1-methylbutyl, 1-ethyl-2-methylbutyl, 1-ethyl-3-methylbutyl, 2-ethyl-1-methylbutyl, 2-ethyl-3-methylbutyl, 1-n-propylbutyl, 1-iso-propylbutyl, 1-iso-propyl-2-methylpropyl, methylcyclohexyl, n-octyl, 1-methylheptyl, 2-methylheptyl, 3-methylheptyl, 4-methylheptyl, 5-methylheptyl, 6-methylheptyl, 1,1-dimethylhexyl, 1,2-dimethylhexyl, 1,3-dimethylhexyl, 1,4-dimethylhexyl, 1,5-dimethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 3,5-dimethylhexyl, 4,4-dimethylhexyl, 4,5-dimethylhexyl, 1-ethylhexyl, 2-ethylhexyl, 3-ethylhexyl, 4-ethylhexyl, 1-n-propylpentyl, 2-n-propylpentyl, 1-iso-propylpentyl, 2-iso-propylpentyl, 1-ethyl-1-methylpentyl, 1-ethyl-2-methylpentyl, 1-ethyl-3-methylpentyl, 1-ethyl-4-methylpentyl, 2-ethyl-1-methylpentyl, 2-ethyl-2-methylpentyl, 2-ethyl-3-methylpentyl, 2-ethyl-4-methylpentyl, 3-ethyl-1-methylpentyl, 3-ethyl-2-methylpentyl, 3-ethyl-3-methylpentyl, 3-ethyl-4-methylpentyl, 1,1,2-trimethylpentyl, 1,1,3-trimethylpentyl, 1,1,4-trimethylpentyl, 1,2,2-trimethylpentyl, 1,2,3-trimethylpentyl, 1,2,4-trimethylpentyl, 1,3,4-trimethylpentyl, 2,2,3-trimethylpentyl, 2,2,4-trimethylpentyl, 2,3,4-trimethylpentyl, 1,3,3-trimethylpentyl, 2,3,3-trimethylpentyl, 3,3,4-trimethylpentyl, 1,4,4-trimethylpentyl, 2,4,4-trimethylpentyl, 3,4,4-trimethylpentyl, 1-n-butylbutyl, 1-iso-butylbutyl, 1-sec-butylbutyl, 1-tert-butylbutyl, 2-tert-butylbutyl, 1-n-propyl-1-methylbutyl, 1-n-propyl-2-methylbutyl, 1-n-propyl-3-methylbutyl, 1-iso-propyl-1-methylbutyl, 1-iso-propyl-2-methylbutyl, 1-iso-propyl-3-methylbutyl, 1,1-diethylbutyl, 1,2-diethylbutyl, 1-ethyl-1,2-dimethylbutyl, 1-ethyl-1,3-dimethylbutyl, 1-ethyl-2,3-dimethylbutyl, 2-ethyl-1,1-dimethylbutyl, 2-ethyl-1,2-dimethylbutyl, 2-ethyl-1,3-dimethylbutyl, 2-ethyl-2,3-dimethylbutyl, 1,2-dimethylcyclohexyl, 1,3-dimethylcyclohexyl, 1,4-dimethylcyclohexyl, ethylcyclohexyl, n-nonyl, 3,5,5-trimethylhexyl and n-decyl group, and other straight, branched or cyclic hydrocarbon groups having 1 to 10 carbon atoms;

a fluoromethyl, trifluoromethyl, chloromethyl, dichloromethyl, trichloromethyl, bromomethyl, dibromomethyl, tribromomethyl, fluoroethyl, chloroethyl, bromoethyl, trifluoroethyl, pentafluoroethyl, tetrachloroethyl and hexafluoro-iso-propyl group, and other straight, branched or cyclic halogenated hydrocarbon groups which have 1 to 21 halogen atoms and 1 to 10 carbon atoms;

a methoxymethyl, ethoxymethyl, propoxymethyl, butoxymethyl, pentoxymethyl, hexyloxymethyl, cyclohexyloxymethyl, methoxyethyl, ethoxyethyl, propoxyethyl, butoxyethyl, pentoxyethyl, hexyloxyethyl, cyclohexyloxyethyl, methoxyethoxyethyl, methoxypropyl, ethoxypropyl, propoxypropyl, butoxypropyl, pentoxypropyl, hexyloxypropyl, cyclohexyloxypropyl and methoxy-ethoxypropyl group, and other alkyl groups which are substituted with straight, branched or cyclic alkoxy groups having 1 to 10 carbon atoms;

a methylthiomethyl, ethylthiomethyl, propylthiomethyl, butylthiomethyl, pentylthiomethyl, hexylthiomethyl, cyclohexylthiomethyl, methylthioethyl, ethylthioethyl, propylthioethyl, butylthioethyl, pentylthioethyl, hexylthioethyl, cyclohexylthioethyl, methoxyethylthioethyl, methylthiopropyl, ethylthiopropyl, propylthiopropyl, butylthiopropyl, pentylthiopropyl, hexylthiopropyl, cyclohexylthiopropyl and methoxyethylthiopropyl group and other alkyl groups which are substituted with straight, branched or cyclic alkylthio gruops having 1 to 10 carbon atoms;

a N-methylaminomethyl, N,N-dimethylaminomethyl, N-ethylaminomethyl, N,N-diethylaminomethyl, N-propylaminomethyl, N,N-dipropylaminomethyl, N-methyl-N-ethylaminomethyl, N-methylaminoethyl, N,N-dimethylaminoethyl, N-ethylaminoethyl, N,N-diethylaminoethyl, N-propylaminoethyl, N,N-dipropylaminoethyl, N-methyl-N-ethylaminoethyl, N-methylaminopropyl, N,N-dimethylaminopropyl, N-ethylaminopropyl, N,N-diethylaminopropyl, N-propylaminopropyl, N,N-dipropylaminopropyl and N-ethyl-N-butylaminopropyl group and other alkyl groups which are substituted with straight, branched or cyclic mono- or di-alkylamino groups having 1 to 10 carbon atoms.

Representative substituted or unsubstituted aryl groups include, for example, a phenyl, naphthyl, anthranyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,6-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 3,4,5-trimethylphenyl, 2-ethylphenyl, propylphenyl, butylphenyl, hexylphenyl, cyclohexylphenyl, octylphenyl, 2-methyl-1-naphthyl, 3-methyl-1-naphthyl, 4-methyl-1-naphthyl, 5-methyl-1-naphthyl, 6-methyl-1-naphthyl, 7-methyl-1-naphthyl, 8-methyl-1-naphthyl, 1-methyl-2-naphthyl, 3-methyl-2-naphthyl, 4-methyl-2-naphthyl, 5-methyl-2-naphthyl, 6-methyl-2-naphthyl, 7-methyl-2-naphthyl, 8-methyl-2-naphthyl and 2-ethyl-1-naphthyl group, and other aryl groups which are substituted with straight, branched or cyclic alkyl groups having 1 to 10 carbon atoms;

a 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 3,6-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxyphenyl, 3,4,5-trimethoxyphenyl, 2-ethoxyphenyl, propoxyphenyl, butoxyphenyl, hextyloxyphenyl, cyclohexyloxyphenyl, octyloxyphenyl, 2-methoxy-1-naphthyl, 3-methoxy-1-naphthyl, 4-methoxy-1-naphthyl, 5-methoxy-1-naphthyl, 6-methoxy-1-naphthyl, 7-methoxy-1-naphthyl, 8-methoxy-1-naphthyl, 1-methoxy-2-naphthyl, 3-methoxy-2-naphthyl, 4-methoxy-2-naphthyl, 5-methoxy-2-naphthyl, 6-methoxy-2-naphthyl, 7-methoxy-2-naphthyl, 8-methoxy-2-naphthyl and 2-ethoxy-1-naphthyl group, and other aryl groups which are substituted with straight, branched or cyclic alkyl groups having 1 to 10 carbon atoms;

a chlorophenyl, dichlorophenyl, trichlorophenyl, bromophenyl, dibromophenyl, iodophenyl, fluorophenyl, difluorophenyl, trifluorophenyl, tetrafluorophenyl, pentafluorophenyl and trifluoromethylphenyl group, and other aryl groups which are substituted with halogen atoms or halogenated alkyl groups;

a N,N-dimethylaminophenyl, N,N-diethylaminophenyl, N-phenyl-N-methylaminophenyl, N-tolyl-N-ethylaminophenyl, N-chlorophenyl-N-cyclohexylaminophenyl and N,N-ditolylaminophenyl group and other aryl groups which are substituted with mono- or disubstituted amino groups;

and a methylthiophenyl, ethylthiophenyl, methylthionaphthyl and phenylthiophenyl group and other alkylthioaryl groups and other arylthioaryl groups.

Representative substituted or unsubstituted alkoxy groups include, for example, a methoxy, ethoxy, propoxy, butoxy, pentoxy, 1-methylbutoxy, 2-methylbutoxy, 3-methylbutoxy, 1,1-dimethylbutoxy, 1,2-dimethylbutoxy, 2,2-dimethylbutoxy, 1-ethylpropoxy, 2-ethylpropoxy, hexyloxy, cyclohexyloxy, heptyloxy, methylcyclohexyloxy, octyloxy, ethylcyclohexyloxy, dimethylcyclohexyloxy, nonyloxy, 2-ethylhexyloxy, 3,5,5-trimethylhexyloxy and decyloxy group, and other straight, branched or cyclic alkoxy groups which have 1 to 10 carbon atoms;

a fluoromethoxy, trifluoromethoxy, fluoroethoxy, trifluoroethoxy, hexafluoroethoxy, fluoropropoxy, trifluoropropoxy, hexafluoropropoxy, chloromethoxy, trichloromethoxy, chloroethoxy and trichloroethoxy group, and other halogenated and straight, branched or cyclic alkoxy groups which have 1 to 21 halogen atoms and 1 to 10 carbon atoms;

a methoxymethoxy, ethoxymethoxy, propoxymethoxy, butoxymethoxy, cyclohexyloxymethoxy, methoxymethoxymethoxy, methoxyethoxy, ethoxyethoxy, propoxyethoxy, butoxyethoxy, cyclohexyloxyethoxy, methoxyethoxyethoxy, ethoxyethoxyethoxy, propoxyethoxyethoxy, butoxyethoxyethoxy, methoxymethylethoxy, ethoxymethylethoxy, propoxymethylethoxy, butoxymethylethoxy, cyclohexyloxymethylethoxy, methoxyethoxymethylethoxy, ethoxyethoxymethylethoxy, propoxyethoxymethylethoxy, butoxyethoxymethylethoxy, 2-[(2'-methoxy)propoxy]propoxy, methoxypropoxy, ethoxypropoxy and propoxypropoxy group, and other straight, branched or cyclic alkoxyalkoxy and alkoxyalkoxyalkoxy groups which have 1 to 10 carbon atoms;

a N-methylaminomethoxy, N,N-dimethylaminomethoxy, N-ethylaminomethoxy, N,N-diethylaminomethoxy, N-methylaminoethoxy, N,N-dimethylaminoethoxy, N-ethylaminoethoxy, N,N-diethylaminoethoxy, N-methylaminopropoxy, N,N-dibutylaminopropoxy and N-methylaminobutoxy group, and other straight, branched or cyclic alkylaminoalkoxy groups which have 1 to 10 carbon atoms;

a methylthiomethoxy, ethylthiomethoxy, propylthiomethoxy, methylthioethoxy, ethylthioethoxy and propylthioethoxy group, and other straight, branched or cyclic alkylthioalkoxy groups which have 1 to 10 carbon atoms;

a phenoxyethoxy, naphthyloxyethoxy, tolyloxyethoxy and ethylphenoxyethoxy group, and other aryloxyalkoxy groups.

Exemplary substituted or unsubstituted aryloxy groups include, for example, a phenyloxy, naphthyloxy, anthranyloxy, 2-methylphenyloxy, 3-methylphenyloxy, 4-methylphenyloxy, 2,3-dimethylphenyloxy, 2,4-dimethylphenyloxy, 2,5-dimethylphenyloxy, 2,6-dimethylphenyloxy, 3,4-dimethylphenyloxy, 3,5-dimethylphenyloxy, 3,6-dimethylphenyloxy, 2,3,4-trimethylphenyloxy, 2,3,5-trimethylphenyloxy, 2,3,6-trimethylphenyloxy, 2,4,5-trimethylphenyloxy, 2,4,6-trimethylphenyloxy, 3,4,5-trimethylphenyloxy, 2-ethylphenyloxy, propylphenyloxy, butylphenyloxy, hexylphenyloxy, cyclohexylphenyloxy, octylphenyloxy, 2-methyl-1-naphthyloxy, 3-methyl-1-naphthyloxy, 4-methyl-1-naphthyloxy, 5-methyl-1-naphthyloxy, 6-methyl-1-naphthyloxy, 7-methyl-1-naphthyloxy, 8-methyl-1-naphthyloxy, 1-methyl-2-naphthyloxy, 3-methyl-2-naphthyloxy, 4-methyl-2-naphthyloxy, 5-methyl-2-naphthyloxy, 6-methyl-2-naphthyloxy, 7-methyl-2-naphthyloxy, 8-methyl-2-naphthyloxy and 2-ethyl-1-naphthyloxy group, and other aryloxy groups which are substituted with straight, branched or cyclic alkyl groups having 1 to 10 carbon atoms;

a 3-methoxyphenyloxy, 4-methoxyphenyloxy, 2,3-dimethoxyphenyloxy, 2,4-dimethoxyphenyloxy, 2,5-dimethoxyphenyloxy, 2,6-dimethoxyphenyloxy, 3,4-dimethoxyphenyloxy, 3,5-dimethoxyphenyloxy, 3,6-dimethoxyphenyloxy, 2,3,4-trimethoxyphenyloxy, 2,3,5-trimethoxyphenyloxy, 2,3,6-trimethoxyphenyloxy, 2,4,5-trimethoxyphenyloxy, 2,4,6-trimethoxyphenyloxy, 3,4,5-trimethoxyphenyloxy, 2-ethoxyphenyloxy, propoxyphenyloxy, butoxyphenyloxy, hexyloxyphenyloxy, cyclohexyloxyphenyloxy, octyloxyphenyloxy, 2-methoxy-1-naphthyloxy, 3-methoxy-1-naphthyloxy, 4-methoxy-1-naphthyloxy, 5-methoxy-1-naphthyloxy, 6-methoxy-1-naphthyloxy, 7-methoxy-1-naphthyloxy, 8-methoxy-1-naphthyloxy, 1-methoxy-2-naphthyloxy, 3-methoxy-2-naphthyloxy, 4-methoxy-2-naphthyloxy, 5-methoxy-2-naphthyloxy, 6-methoxy-2-naphthyloxy, 7-methoxy-2-naphthyloxy, 8-methoxy-2-naphthyloxy and 2-ethoxy-1-naphthyloxy group, and other aryloxy groups which are substituted with straight, branched or cyclic alkoxy groups having 1 to 10 carbon atoms;

a chlorophenyloxy, dichlorophenyloxy, trichlorophenyloxy, bromophenyloxy, dibromophenyloxy, iodophenyloxy, fluorophenyloxy, difluorophenyloxy, trifluorophenyloxy, tetrafluorophenyloxy and pentafluorophenyloxy group, and other aryloxy groups which are substituted with halogen atoms;

a trifluoromethylphenyloxy group and other aryloxy groups which are substituted with halogenated alkyl groups;

a N,N-dimethylaminophenyloxy, N,N-diethylaminophenyloxy, N-phenyl-N-methylaminophenyloxy, N-tolyl-N-ethylaminophenyloxy, N-chlorophenyl-N-cyclohexylaminophenyloxy and N,N-ditrylaminophenyloxy group, and other N-mono or N,N-disubstituted aminoaryloxy groups;

a methylthiophenyloxy, ethylthiophenyloxy, methylthionaphthyloxy and cyclohexylthoiphenyloxy and other alkylthioaryloxy groups; and a phenylthiophenyloxy, naphthylthiophenyloxy and phenylthionaphthyloxy group and other arylthioaryloxy groups.

Representative substituted or unsubstituted N-alkylamino group include, for example, a N-methylamino, N-ethylamino, N-n-propylamino, N-iso-propylamino, N-n-butylamino, N-iso-butylamino, N-sec-butylamino, N-n-pentylamino, N-1-methylbutylamino, N-2-methylbutylamino, N-3-methylbutylamino, N-1,1-dimethylbutylamino, N-1,2-dimethylbutylamino, N-2,2-dimethylbutylamino, N-1-ethylpropylamino, N-2-ethylpropylamino, N-n-hexylamino, N-cyclohexylamino, N-n-heptylamino, N-methylcyclohexylamino, N-n-octylamino, N-2-ethylhexylamino, N-ethylcyclohexylamino, N-dimethylcyclohexylamino, N-n-nonylamino, N-3,5,5-trimethylhexylamino and N-n-decylamino group, and other straight, branched or cyclic alkylamino groups having 1 to 10 carbon atoms;

a N-methoxymethylamino, N-ethoxymethylamino, N-methoxyethylamino, N-ethoxyethylamino, N-n-propoxyethylamino, N-iso-propoxyethylamino, N-n-butoxyethylamino, N-iso-butoxyethylamino, N-tert-butoxyethylamino, N-n-hexyloxyethylamino, N-cyclohexyloxyethylamino, N-2-methoxypropylamino, N-methoxy-iso-propylamino, N-2-ethoxypropylamino, N-ethoxy-iso-propylamino, N-2-propoxypropylamino and N-propoxy-iso-propylamino group, and other straight, branched or cyclic alkoxyalkylamino groups having 1 to 10 carbon atoms;

a N-methylthiomethylamino, N-ethylthiomethylamino, N-methylthioethylamino, N-ethylthioethylamino, N-n-propylthioethylamino, N-iso-propylthioethylamino, N-n-butylthioethylamino, N-iso-butylthioethylamino, N-tert-butylthioethylamino, N-n-hexylthioethylamino, N-cyclohexylthioethylamino, N-2-methylthiopropylamino, N-methylthio-iso-propylamino, N-2-ethylthiopropylamino, N-ethylthio-iso-propylamino, N-2-propylthiopropylamino, N-propylthio-iso-propylamino, N-methylthioethoxyethylamino and N-ethylthioethylthioethylamino group, and straight, branched or cyclic alkylthioalkylamino groups having 1 to 10 carbon atoms;

a N-methylaminomethylamino, N-methylaminoethylamino, N-ethylaminomethylamino, N-ethylaminoethylamino, N,N-dimethylaminomethylamino, N,N-diethylaminomethylamino, N,N-dimethylaminoethylamino and N,N-diethylaminoethylamino group, and other straight, branched and cyclic N-alkylaminoalkylamino groups and N,N-dialkylaminoalkylamino group.

Exemplary substituted or unsubstituted N,N-dialkylamino groups include, for example, a N,N-dimethylamino, N,N-diethylamino, N,N-di(n-propyl)amino, N,N-di(iso-propyl)amino, N,N-di(n-butyl)amino, N,N-di(iso-butyl)amino, N,N-di(sec-butyl)amino, N,N-di(n-pentyl)amino, N,N-di(1-methylbutyl)amino, N,N-di(2-methylbutyl)amino, N,N-di(3-methylbutyl)amino, N,N-di(1,1-dimethylbutyl)amino, N,N-di(1,2-dimethylbutyl)amino, N,N-di(2,2-dimethylbutyl)amino, N,N-di(1-ethylpropyl)amino, N,N-di(2-ethylpropyl)amino, N,N-di(n-hexyl)amino, N,N-di(cyclohexyl)amino, N,N-di(n-heptyl)amino, N,N-di(methylcyclohexyl)amino, N,N-di(n-octyl)amino, N,N-di(2-ethylhexyl)amino, N,N-di(dimethylcyclohexyl)amino, N,N-di(n-nonyl)amino, N,N-di(3,5,5-trimethylhexyl)amino, N,N-di(n-decyl)amino, N-methyl-N-ethylamino, N-propyl-N-ethylamino, N-hexyl-N-ethylamino, N-octyl-N-ethylamino, N-cyclohexyl-N-ethylamino group and other dialkylamino groups which are substituted with straight, branched or cyclic alkyl groups having 1 to 10 carbon atoms;

a N,N-di(methoxymethyl)amino, N,N-di(ethoxymethyl)amino, N,N-di(methoxyethyl)amino, N,N-di (ethoxyethyl)amino, N,N-di(n-propoxyethyl)amino, N,N-di(iso-propoxyethyl)amino, N,N-di(n-butoxyethyl)amino, N,N-di(iso-butoxyethyl)amino, N,N-di(tert-butoxyethyl)amino, N,N-di(n-hexyloxyethyl)amino, N,N-di(cyclohexyloxyethyl) amino, N,N-di(2-methoxypropyl)amino, N,N-di(methoxy-iso-propyl)amino, N,N-di(2-ethoxypropyl)amino, N,N-di(ethoxy-iso-propyl)amino, N,N-di(2-propoxypropyl)amino, N,N-di(propoxy-iso-propyl)amino, N,N-di(methoxyethoxyethyl)amino, N,N-di(ethoxyethoxyethyl)amino, N-methyl-N-methoxyethylamino, N-propyloxyethyl-N-ethylamino, N-hexyloxyethyl-N-ethylamino, N-ethoxyethoxyethyl-N-ethylamino and N-cyclohexyloxyethyl-N-ethylamino group, and other dialkylamino groups which are su bstituted with straight, branched or cyclic alkoxy groups;

a N,N-di(methylthiomethyl)amino, N,N-di(ethylthiomethyl)amino, N,N-di(methylthioethyl)amino, N,N-di(ethylthioethyl)amino, N,N-di(n-propylthioethyl)amino, N,N-di(iso-propylthioethyl) amino, N,N-di(n-butylthioethyl)amino, N,N-di(iso-butylthioethyl)amino, N,N-di(tert-butylthioethyl) amino, N,N-di(n-hexylthioethyl)amino, N,N-di(cyclohexylthioethyl)amino, N,N-di(2-methylthiopropyl)amino, N,N-di(methylthio-iso-propyl)amino, N,N-di(2-ethylthiopropyl)amino, N,N-di(ethylthio-iso-propyl)amino, N,N-di(2-propylthiopropyl)amino, N,N-di(propylthio-iso-propyl)amino, N,N-di(methylthioethoxyethyl)amino and N,N-di(ethylthioethylthioethyl)amino group, and other N,N-dialkylthioalkylamino groups which are substituted with straight, branched or cyclic alkoxy groups;

a N,N-di(N-methylaminomethyl)amino, N,N-di(N-methylaminoethyl)amino, N,N-di(N-ethylaminomethyl)amino, N,N-di(N-ethylaminoethyl) amino, N,N-di(N,N-dimethylaminomethyl)amino, N,N-di(N,N-diethylaminomethyl)amino, N,N-di(N,N-dimethylaminoethyl)amino and N,N-di(N,N-diethylaminoethyl) amino group, and other N,N-di(N-alkylaminoalkyl)amino groups, and N,N-di(N,N-dialkylaminoalkyl)amino groups which have 1 to 10 carbon atoms.

Representative substituted or unsubstituted N-arylamino groups include, for example, a N-phenylamino, N-tolylamino, N-chlorophenylamino, N-trifluorophenylamino, N-naphthylamino, N-methylnaphthylamino and N-chloronaphthylamino group.

Exemplary substituted or unsubstituted N,N-diarylamino group include, for example, a N,N-diphenylamino, N,N-ditolylamino, N,N-dichlorophenylamino, N,N-ditrifluorophenylamino, N,N-dinaphthylamino, N,N-dimethylnaphthylamino and N,N-dichloronaphthylamino group.

Exemplary substituted or unsubstituted N-alkyl-N-arylamino group include a N-methyl-N-phenylamino, N-ethyl-N-tolylamino, N-methoxyethyl-N-chlorophenylamino, N-ethyl-N-trifluorophenylamino, N-cyclohexyl-N-naphthylamino, N-ethyl-N-naphthylamino, N-2-ethylhexyl-N-methylnaphthylamino, N-methyl-N-chloronaphthylamino group.

Substituents of $R^1$ to $R^{10}$ are preferably a hydrogen, fluorine, chlorine and bromine atom and a hydroxy, amino, methyl, ethyl, propyl, trifluoromethyl, phenyl, N,N-dimethylamino, N,N-diphenylamino and N,N-ditolylamino group.

Substituents of $R^{11}$ to $R^{60}$ are preferably and $Y^1$ to $Y^{10}$ are preferably a hydrogen, fluorine, chlorine and bromine atom, and a nitro, amino, hydroxy, methyl, ethyl and trifluoromethyl group, and phenyl group.

Preferred $X^1$ and $X^2$ are fluorine, chlorine and bromine atom.

In the processes of the invention, specific examples of the organic basic solvent used in Process A include, N,N-dimethylaniline, N,N-diethylaniline, N-methylaniline, N-ethylaniline and other aniline derivatives; pyridine and other pyridine derivatives; quinoline, methylquinoline, isoquinoline and other quinoline derivatives; diazabicycloundecene, diazabicyclononene, N-ethylmorpholine and other cyclic amine derivatives. In these solvents, N,N-dimethylaniline and N,N-diethylaniline are preferably used. The solvents can be used singly or as a mixture. The amount of the solvent is 1 to 50 parts by weight, preferably 4 to 21 parts by weight for a part of the quinoline derivative of the formula (5).

In the processes of the invention, specific examples of the organic solvent used in Process D, Process E and Process G include N,N-dimethylaniline, N,N-diethylaniline, N-methylaniline, N-ethylaniline and other aniline derivatives; pyridine and other pyridine derivatives; quinoline, methylquinoline, isoquinoline and other quinoline derivatives; toluene, xylene and other aromatic hydrocarbons chlorobenzene, dichlorobenzene and other halogenated aromatic hydrocarbons; and nitrobenzene and other nitroaromatic hydrocarbons. Preferred solvents are N,N-dimethylaniline, N,N-diethylaniline, dichlorobenzene and quinoline. These solvents can be used singly or as a mixture. The amount of the solvent is 1 to 50 parts by weight, preferably 4 to 16 parts by weight for a part by weight of the quinoline derivative of the formula (5) or the quinoline compound of the formula (4).

In the processes of the invention, specific examples of organic amine for use in Process F include, pyridine, picoline, lutidine and other pyridine derivatives; quinoline, isoquinoline and other quinoline derivatives; diazabicyclo-undecene, diazabicyclo-nonene, N-methylmorpholine, N,N'-dimethylmorpholine, N-methylpiperidine, N,N'-dimethylpiperidine and other nitrogen heterocyclic compounds. Pyridine, picoline and butidine are preferably used in these organic amines, and can be used singly or as a mixture. The amount of the organic amine is 3 to 100 parts by weight, preferably 5 to 50 parts by weight for a part by weight of the zinc halogenide complex of the formula (2).

In the processes of the invention, specific examples of inorganic acids which can be used in Process A, Process B and Process C include hydrochloric acid, sulfuric acid, nitric acid and phosphoric acid. Hydrochloric acid and sulfuric acid are preferably used in these inorganic acids. The amount in Process A is 1 to 200 molar ratio, preferably 6 to 35 molar ratio to the amount of the quinoline derivative of the formula (5). The amount in Process B is 2 to 200 molar ratio to the amount of the zinc halogenide complex of the formula (2). The amount in Process C is 2 to 200 molar ratio to the amount of the zinc complex of the formula (3). When a compound which forms salt with inorganic acid is present as in the case of organic basic solvent and organic solvent, the inorganic acid is required in excess.

In the processes of the invention, specific examples of zinc halogenide which are used in Process A, Process D, Process E and Process G include zinc fluoride, zinc chloride, zinc bromide and zinc iodide. Zinc chloride and zinc bromide are preferably used. The amount in Process A, Process D and Process G is 0.1 to 50 molar ratio, preferably 0.5 to 10 molar ratio to the amount of the quinoline derivative of the formula (5). The amount in Process E is 0.1 to 50 molar ratio, preferably 0.2 to 10 molar ratio, more preferably 0.5 to 2.5 molar ratio to the amount of the quinoline compound of the formula (4).

In the processes of the invention, the amount of the phthalimide derivative of the formula (6) which is used in Process A is 0.2 to 10 molar ratio, preferably 0.5 to 2 molar ratio, more preferably 1.1 to 2.0 molar ratio to the amount of the quinoline derivative of the formula (5). When the quinoline derivative is used in excess, residual quinoline derivative or impurity of the same cannot be removed satisfactorily and is liable to reduce fluorescence property of the quinoline compound of the formula (4). The amount of the phthalimide derivative which is used in Process D and Process G is 0.2 to 10 molar ratio, preferably 0.5 to 2 molar ratio to the amount of the quinoline derivative of the formula (5).

In the processes of the invention, the reaction temperature with zinc halogenide in Process A, Process D and Process E is usually 100 to 250° C., preferably 130 to 180° C. The reaction time is usually 5 to 50 hours. The reaction temperature with zinc halogenide in Process G is usually 100 to 250° C., preferably 110 to 180° C. The reaction time is usually 5 to 50 hours.

In the processes of the invention, the temperature for treating with the inorganic acid in Process A, Process B and Process C is usually 50 to 100° C., preferably 80 to 95° C. The treating time is usually 0.1 to 10 hours.

In the processes of the invention, the temperature for heating with the organic amine in Process F is 30~200° C., preferably 50~150° C. The treating time is usually 0.1~10 hours.

As to the post-treatment after finishing the reaction in Process A, Process B and Process C, precipitated solid is filtered as intact, washed and dried, and subjected to purification such as sludging with a polar solvent or recrystallization, when necessary. In Process D, Process E, Process F and Process G, the precipitated solid is filtered as intact or after removing the solvent by distillation, washed, dried and, when necessary, purified by sludging with a polar solvent.

The quinoline compound of the formula (7) obtained by the process of the invention is a crystal having a peak at least at a Bragg angle (2 θ) of 12.8°, 15.2°, 18.3°, 22.5°, 25° and 28.4°. Particularly, the crystal where the intensity ratio of the peak at 12.8° is 0.7 or less to the peak at 15.2° has brightness of 180% or more in the solid state for the brightness of Lumogen Brilliant Yellow and is thus a compound being excellent in luminescent property.

Preparation process of electro electro luminescence element has been known in the description of Japanese Laid-Open Patent SHO 58-194393, J. Appl. Phys. Lett., 51(12), 913(1987), and 65(7), 3610(1989), and Japan Journal of Applied Physics, vol. 27, No.2, line 269(1998), and vol. 27, No.4. line 71(1988).

Figure 9:
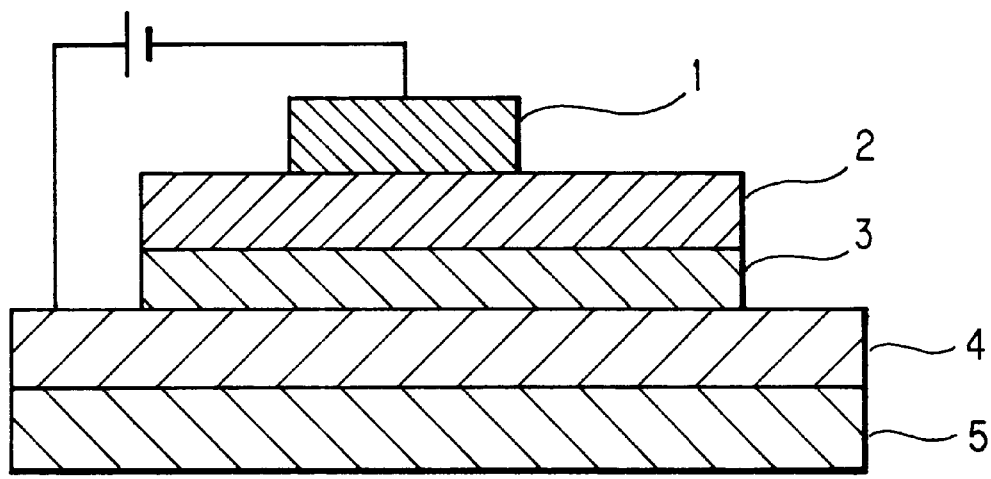
FIG. 9 is a drawing which shows one embodiment of the EL element to be applied the compound of the invention.

As shown in FIG. 9 in detail, the EL element has structure wherein as anode (4), positive hole transporting layer (3) which is composed of an organic compound, luminescent layer (2) which consists of the compound of the invention, and a metal cathode (1) are successively stacked up on a glass substrate (ITO glass substrate) (5).

Figure 10:
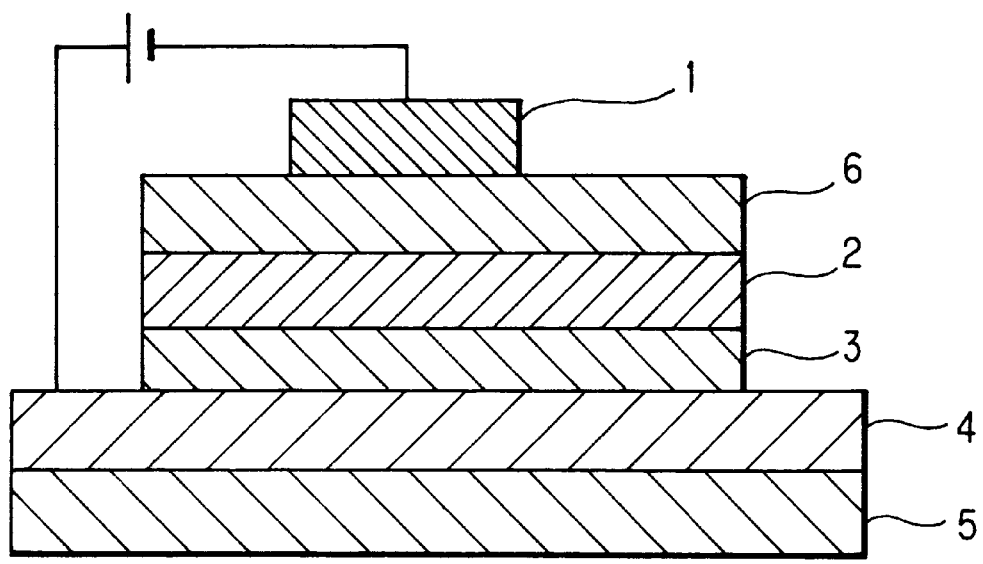
FIG. 10 is a drawing which shows another embodiment of the EL element to be applied the compound of the invention.

Further, as shown in FIG. 10, the EL element can also have structure wherein an anode (4), positive hole transporting layer (3) which is composed of an organic compound, luminescent layer (2) which consists of the compound of the invention, electron transporting layer (6) and a metal cathode (1) are successively stacked up on a glass substrate (ITO glass substrate) (5).

The positive hole transporting compounds which can be used for the positive hole transporting layer (3) in the above structure of the element are compounds containing tertiary amine which bonds to one or more aromatic rings, or other low-molecular weight compounds or high polymers which have positive hole transporting property. The transporting compounds are preferably triphenylamine derivatives represented by the formula (8) or the formula (9), or pyrazoline derivative, polyvinyl carbazole and polysilane. These compounds can be used singly or as a mixture.

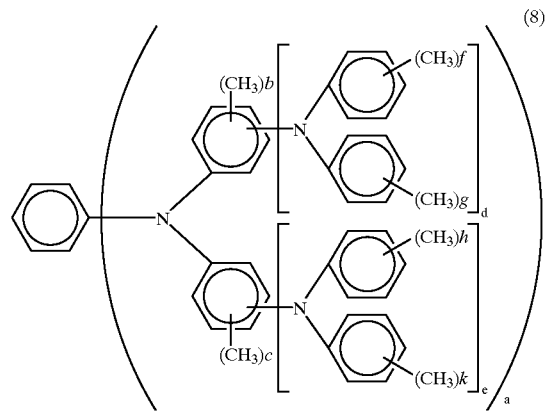

(8)

where each of a, b, c, d, e, f, g, h, and k is individually 0 or an integer of 1, 2, or 3.

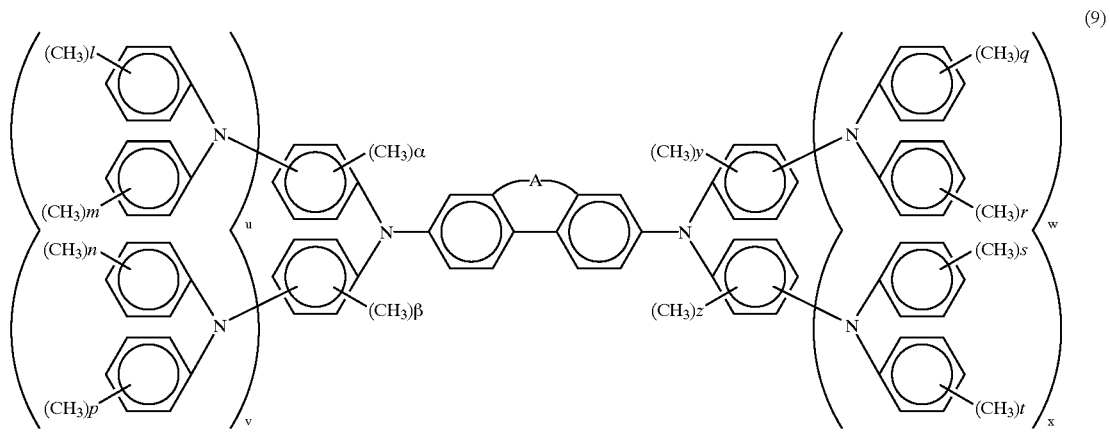

where each of l, m, n, p, q, r, s, t, u, v, w, x, y, z, α, and β is individually 0 or 1; and A is a non-ring forming divalent hydrogen atom, —CH$_2$—, or —C(CH$_3$)$_2$—.

The materials used for the anode of the EL element in the invention preferably have a work function as large as possible and include, for example, nickel, gold, platinum, palladium, selenium, iridium, an alloy of these metals, tin oxide, ITO, and copper iodide. Polyphenylene sulfide, polyaniline and other conductive polymers can also be used.

On the other hand, the materials used for the cathode preferably have a small work function and include, for example, silver, lead, tin, magnesium, aluminum, calcium, indium, chromium, lithium and an alloy of these metals. One of a pair of materials used for the anode and cathode desirably has transmittance of 50% or more in the oscillating wave length region of the element.

Glass and a plastic film can be used for a substrate of transparent electrodes which are used in the invention.

The present invention will be further illustrated by way of examples hereinafter. However, the invention is not limited to the following examples unless exceeding the subject matter.

EXAMPLE 1

Experimental Example for Process A

To a reaction vessel, 15 g (0.102 mole) of phthalimide, 7.3 g (0.051 mole) of quinaldine, 29.2 g (0.214 mole) of zinc chloride and 150 g of N,N-dimethylaniline were charged and heated under nitrogen ventilation at 150° C. for 30 hours. The reaction mixture was poured into 650 g of a 10% aqueous hydrochloric acid solution and treated at 95° C. for 1 hour.

After cooling to 50° C., the mixture was filtered and washed with water. The filter cake was dried to obtain 11.9 g of the quinoline compound having the formula (7).

The compounds (7) had purity of 100% and purity reduced yield for quinaldine was 86%.

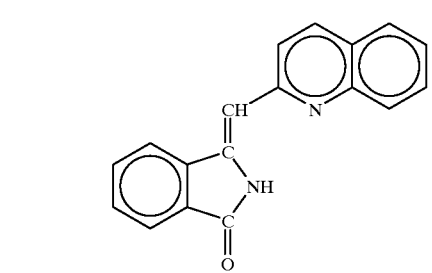

The X-ray diffraction spectrum of the compound (7) is shown in FIG. 1. The peak intensity ratio at Bragg angle 12.8° was 0.46 for the intensity at Bragg angle 15.2°. The crystal was measured in the solid state as intact with a fluorophotometer: UM-2S, manufactured by Hekisa Kagaku Co. The crystal had brightness of 220% for the brightness of Lumogen Brilliant Yellow.

EXAMPLE 2

Experimental Example for Process A

To a reaction vessel, 15 g (0.102 mole) of phthalimide, 13.2 g (0.0923 mole) of quinaldine, 29.2 g (0.214 mole) of zinc chloride and 150 g of N,N-dimethylaniline were charged and heated under nitrogen ventilation at 150° C. for 30 hours. The reaction mixture was poured into 650 g of a 10% aqueous hydrochloric acid solution and treated at 95° C. for 1 hour. After cooling to 50° C., the mixture was filtered and washed with water. The filter cake was dried to obtain 19.4 g of the quinoline compound having the formula (7).

The compounds had purity of 100% and purity reduced yield for phthalimide was 77%.

Figure 2:
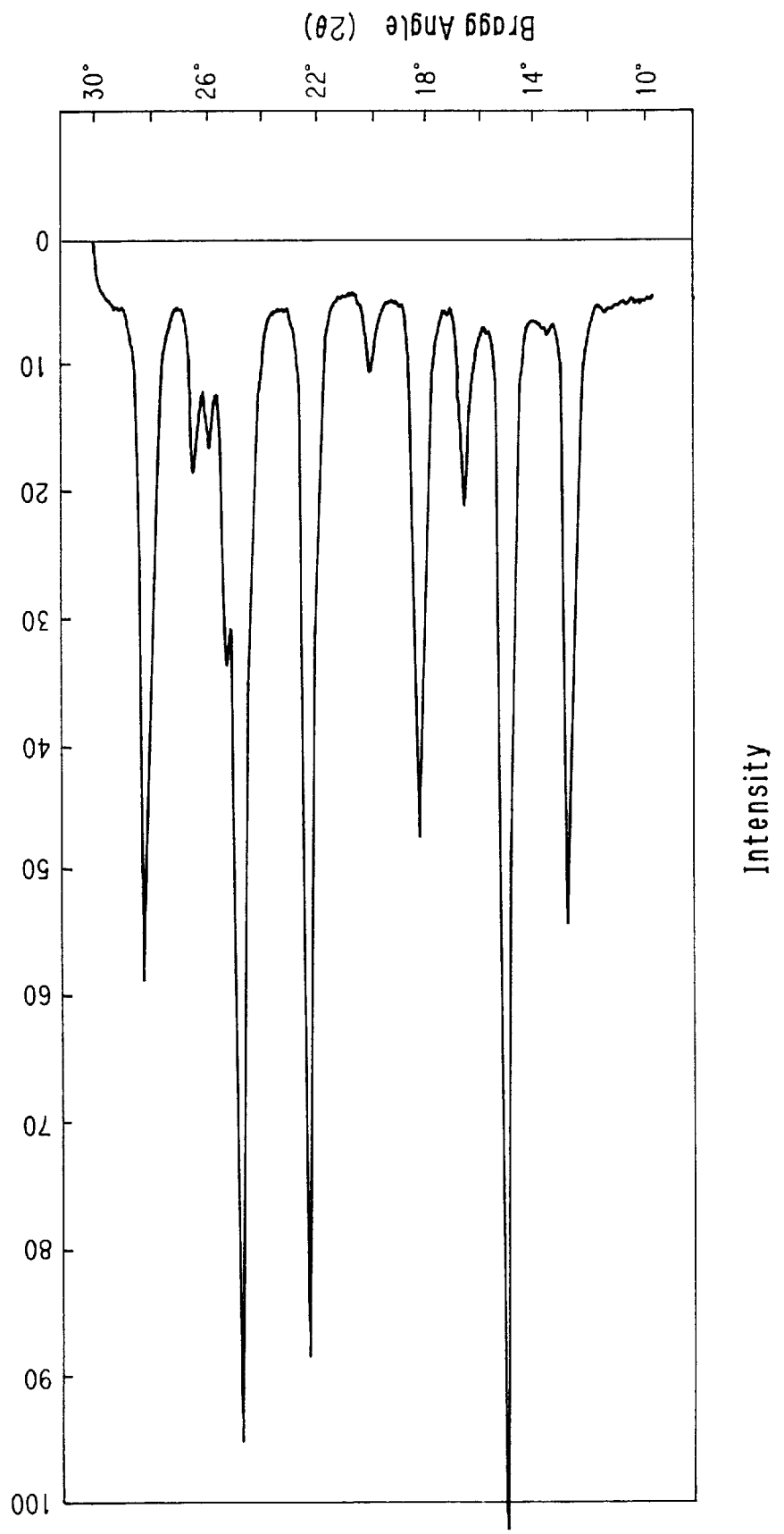
FIG. 2 is a X-ray diffraction spectrum of the quinoline compound obtained in Example 2 and shown by the formula (7).

The X-ray diffraction spectrum of the compound is shown in FIG. 2. The peak intensity ratio at Bragg angle 12.8° was 0.46 for the intensity at Bragg angle 15.2°. The crystal was measured in the solid state as intact with a fluorophotometer: UM-2S, manufactured by Hekisa Kagaku Co. The crystal has brightness of 204% for the brightness of Lumogen Brilliant Yellow.

EXAMPLE 3

Experimental Example for Process A

To a reaction vessel, 15 g (0.102 mole) of phthalimide, 14.6 g (0.102 mole) of quinaldine, 29.2 g (0.214 mole) of zinc chloride and 150 g of N,N-dimethylaniline were charged and heated under nitrogen ventilation at 150° C. for 30 hours. The reaction mixture was poured into 650 g of a 10% aqueous hydrochloric acid solution and treated at 95° C. for 1 hour. After cooling to 50° C., the mixture was filtered and washed with water. The filter cake was dried to obtain 20.9 g of the quinoline compound having the formula (7).

The compounds had purity of 100% and purity reduced yield for phthalimide was 75%.

Figure 3:
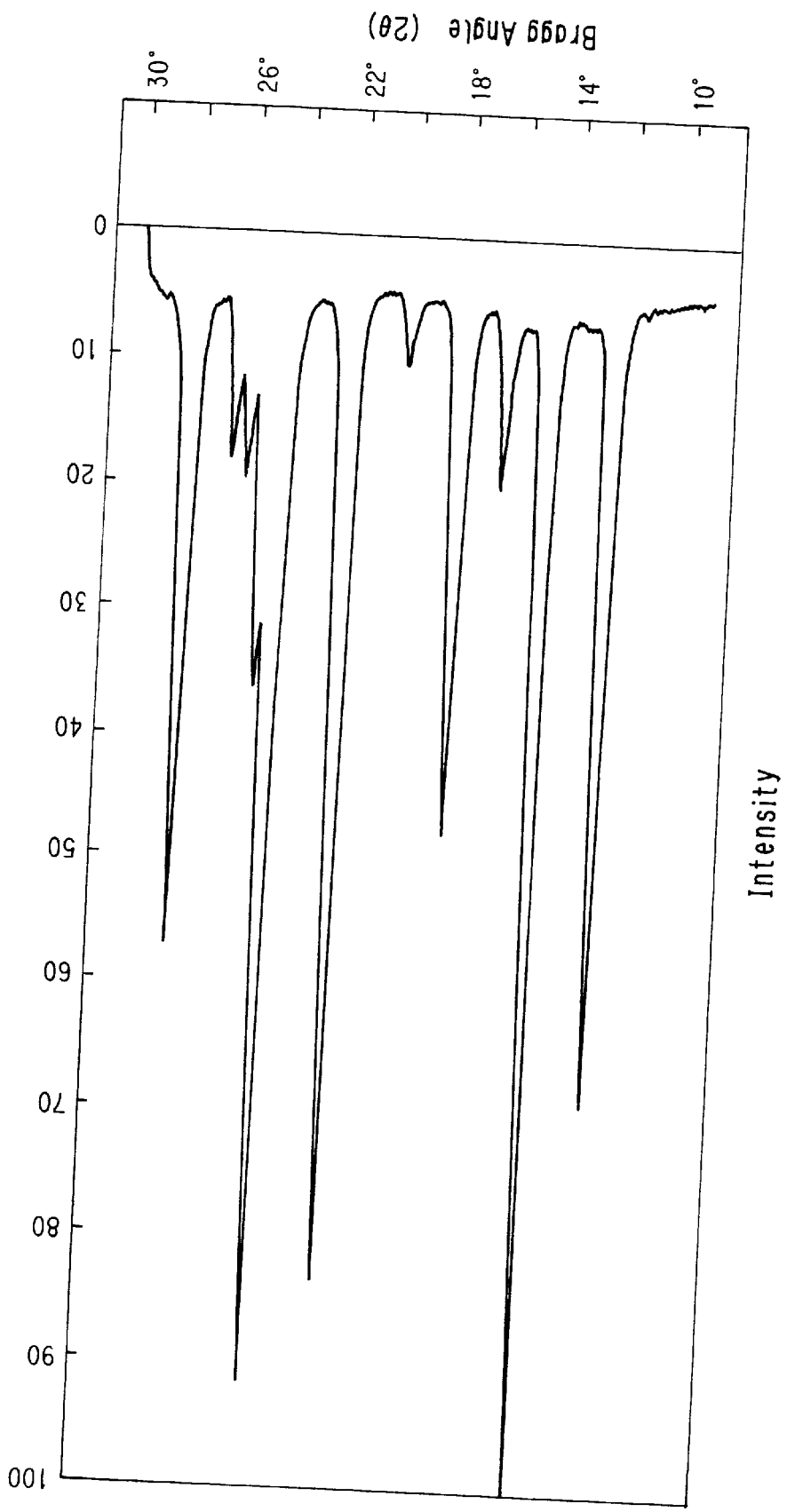
FIG. 3 is a X-ray diffraction spectrum of the quinoline compound obtained in Example 3 and shown by the formula (7).

The X-ray diffraction spectrum of the compound is shown in FIG. 3. The peak intensity ratio at Bragg angle 12.8° was 0.70 for the intensity at Bragg angle 15.2°. The crystal was measured in the solid state as intact with a fluorophotometer: UM-2S, manufactured by Hekisa Kagaku Co. The crystal had brightness of 189% for the brightness of Lumogen Brilliant Yellow.

EXAMPLE 4

Preparation Example 4

Experimental Example for Process A

To a reaction vessel, 50.0 g (0.340 mole) of phthalimide, 97.3 g (0.680 mole) of quinaldine, 99.0 g (0.726 mole) of zinc chloride and 400 g of N,N-dimethylaniline were charged and heated under nitrogen ventilation at 180° C. for 10 hours. The reaction mixture was poured into 1720 g of a 10% aqueous hydrochloric acid solution and treated at 100° C. for 1 hour. After cooling to a room temperature, the mixture was filtered and washed with 2000 g of methanol. The filter cake was sludged with 500 g of methanol, the mixture was filtered and washed with methanol and then the filter cake was dried to obtain 80 g of the quinoline compound having the formula (7).

The compounds had purity of 97% and purity reduced yield for phthalimide was 84%.

Figure 4:
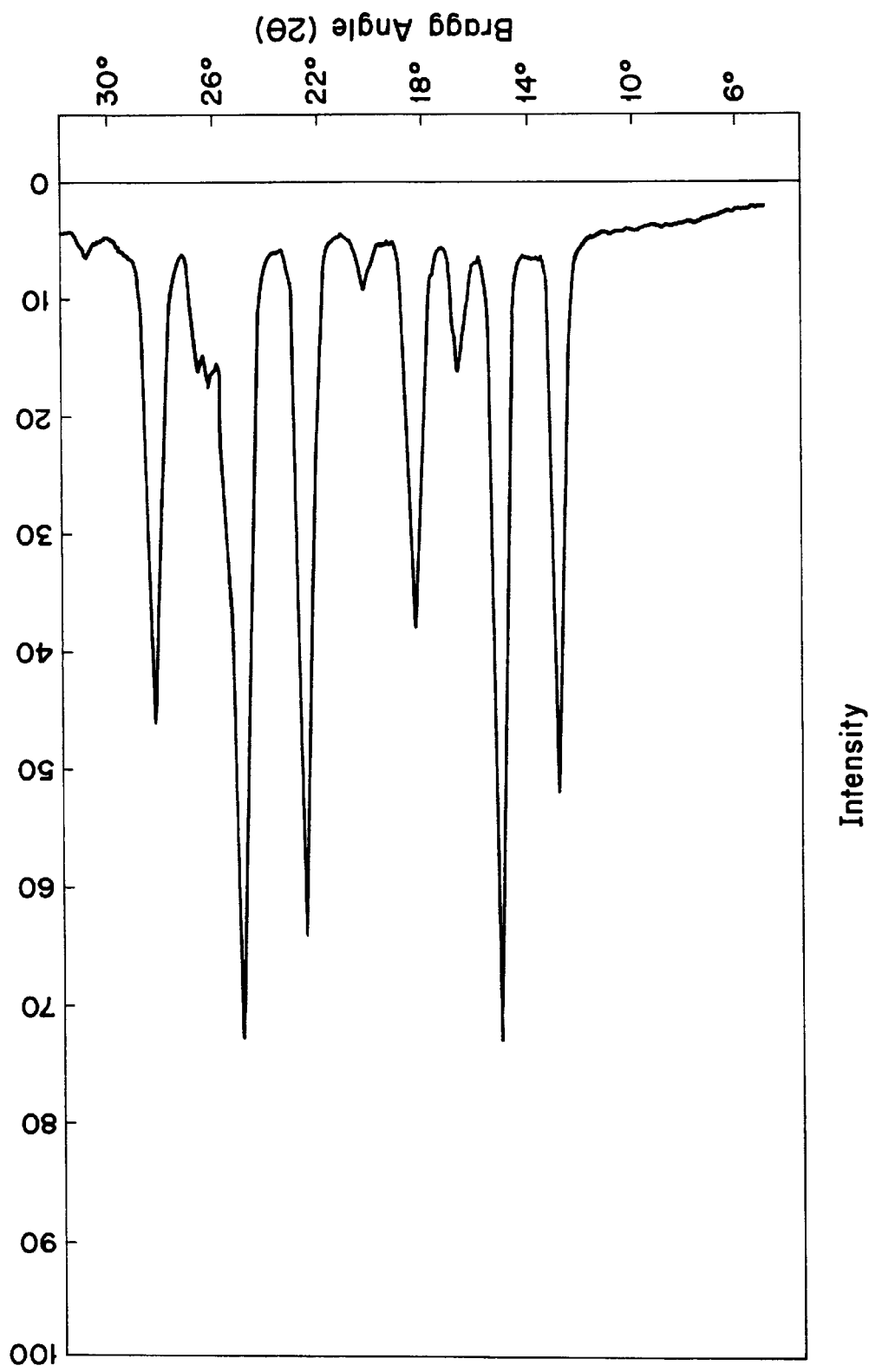
FIG. 4 is a X-ray diffraction spectrum of the quinoline compound obtained in Example 4 and shown by the formula (7).

The X-ray diffraction spectrum of the compound is shown in FIG. 4. The peak intensity ratio at Bragg angle 12.8° was 0.70 for the intensity at Bragg angle 15.2°. The crystal was measured in the solid state as intact with a fluorophotometer: UM-2S, manufactured by Hekisa Kagaku Co. The crystal had brightness of 180% for the brightness of Lumogen Brilliant Yellow.

(EL Element Preparation Example-4)

On an ITO glass substrate, N,N'-diphenyl-N,N'-ditolyl-1,1-diphenyl-4,4'-diamine was stacked to a film thickness of 50 nm under vacuum of $5 \times 10^{-5}$ torr by a resistance heating method. Successively, the quinoline compound of the formula (7) was stacked to a film thickness of 50 nm and further, an aluminum electrode was deposited to a film thickness of 150 nm under vacuum of $6 \times 10^{-5}$ torr. A positive electric field was applied to the ITO side of the element and a negative electric field was applied to the aluminum side. The emission from the surface of ITO glass substrate of the element was observed. As a voltage of 19V and a current density of 26 mA/cm$^2$, the emission was green and stable and the brightness was 115 Cd/m$^2$.

(Fluorescent Material Preparation Example-4)

The compound of the formula (7) was added to polyethylene terephthalate resin powder, hot pressed at 280° C. and cooled to obtain a sheet having thickness of 0.5 mm. The sheet was measured with a fluorophotometer: FP-770, manufactured by Nippon Bunko Co. λ em was 523 nm.

EXAMPLE 5

Experimental Example for Process A

To a reaction vessel, 10 g (0.068 mole) of phthalimide, 18.74 g (0.136 mole) of quinaldine, 23.6 g (0.173 mole) of zinc chloride and 250 g of N,N-dimethylaniline were charged and heated under nitrogen ventilation at 150° C. for 10 hours. The reaction mixture was poured into 640 g of a 10% aqueous hydrochloric acid solution and treated at 100° C. for 1 hour. After cooling to 40° C., the solid portion was filtered, washed with water and dried to obtain 15.0 g of the quinoline compound having the formula (7). Purity of the compound was 98.2% and purity reduced yield was 80% for phthalimide.

EXAMPLE 6

Preparation Example 6

Experimental Example for Process A

After suspending 92.5 g (0.497 mole) of 6-isopropylquinaldine and 48 g (0.25 mole) of 3-nitrophthalimide in 384 g of N,N-dimethylaniline, 72.3 g (0.53 mole) of zinc chloride was added. The mixture was heated under nitrogen ventilation at 150° C. for 10 hours. The reaction mixture was poured into 1265 g of a 10% aqueous hydrochloric acid solution and treated at 100° C. for an hour. After cooling to 40° C., the solid portion was filtered, washed with water and dried to obtain 69.6 g of the quinoline compound having the formula (10).

The purity was 97% and the purity reduced yield was 75% for 3-nitrophthalimide.

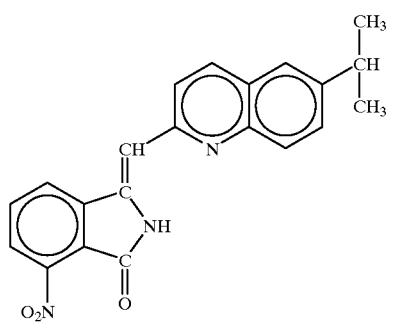

(10)

The result of MS spectrum was as follow; m/e=358

Following results were obtained by elemental analysis.

|  | C | H | N |
| --- | --- | --- | --- |
| Calculated (%) | 70.4 | 4.5 | 11.7 |
| Found (%) | 70.1 | 4.8 | 11.3 |

(EL Element Preparation Example-6)

On an ITO glass substrate, N,N'-diphenyl-N,N'-ditolyl-1,1-diphenyl-4,4'-diamine was stacked to a film thickness of 50 nm under vacuum of $5 \times 10^{-5}$ torr by a resistance heating method. Successively, the quinoline compound of the formula (10) was stacked to a film thickness of 50 nm and further, an aluminum electrode was deposited to a film thickness of 150 nm under vacuum of $6 \times 10^{-5}$ torr. A positive electric field was applied to the ITO side of the element and a negative electric field was applied to the aluminum side. The emission from the surface of ITO glass substrate of the element was observed. As a voltage of 19V and a current density of 26 mA/cm$^2$, the emission was green and stable and the brightness was 115 Cd/m$^2$.

(Fluorescent Material Preparation Example-6)

The quinoline compound of the formula (10) was added to polyethylene terephthalate resin powder, hot pressed at 280° C. and cooled to obtain a sheet having thickness of 0.5 mm. The sheet was measured with a fluorophotometer: FP-770, manufactured by Nippon Bunko Co. Emission at 520 nm and excitation at 375 nm were obtained.

EXAMPLE 7

Preparation Example-7

Experimental Example of Process A

To a reaction vessel, 219 g (1.00 mole) of 5-phenylquinaldine, 143 g (0.502 mol) of 3,4,5,6-tetrachlorophthalimide, 136 g (0.604 mole) of zinc bromide and 2000 g of N,N-diethylaniline were charged and heated under nitrogen ventilation at 180° C. for 15 hours. The reaction mixture was poured into 10 liter of a 5% aqueous hydrochloric acid solution and treated at 80° C. for 2 hours. After cooling to room temperature, the solid portion was filtered, washed with 4000 g of methanol, sludged with 1000 g of methanol, filtered, washed with methanol, and dried to obtain 220 g of the quinoline compound having the formula (11). Purity was 98% and the purity reduced yield was 88% for 3,4,5,6-tetrachlorophthalimide

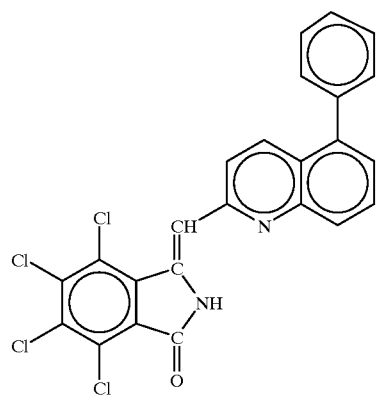

(11)

Result of MS spectrum was as follows; m/e=486
Following results were obtained by elemental analysis.

|  | C | H | N | Cl |
|---|---|---|---|---|
| Calculated (%) | 59.3 | 2.5 | 5.8 | 29.2 |
| Found (%) | 58.9 | 2.5 | 5.7 | 29.1 |

(EL Element Preparation Example-7)

On a glass substrate which formed an ITO transparent electrode, 1,1-bis(4-N,N-ditolylaminophenyl)cyclohexanone was stacked to a film thickness of 50 nm. Successively, the quinoline compound of the formula (11) was stacked to a film thickness of 50 nm and further, 2,2',6,6'-tetramethylphenoquinone was stacked to a film thickness of 50 nm. A back electrode was formed by stacking indium to a film thickness of 150 nm. When a voltage of 8V was applied, emission of 280 Cd/m² was obtained.

(Fluorescent Material Preparation Example-7)

The quinoline compound of the formula (11) was added to polyethylene terephthalate resin powder, hot pressed at 280° C. and cooled to obtain a sheet having thickness of 0.5 mm. The sheet was measured with a fluorophotometer: FP-770, manufactured by Nippon Bunko Co. Emission at 530 nm and excitation at 383 nm were obtained.

EXAMPLE 8

Preparation Example-8

Experimental Example for Process A

To a reaction vessel, 338 g (1.00 mole) of 6-N,N-ditolylaminoquinaldine, 95 g (0.508 mol) of 3-ethoxyphthalimide, 183 g (0.997 mole) of zinc acetate and 6000 g of o-dichlorobenzene were charged and heated under nitrogen ventilation at 180° C. for 15 hours. The reaction mixture was poured into 10 liter of a 5% aqueous hydrochloric acid solution and treated at 80° C. for 2 hours. After cooling to room temperature, the solid portion was filtered, washed with 5000 g of methanol, sludged with 4000 g of methanol, filtered, washed with methanol, and dried to obtain 200 g of the quinoline compound having the formula (12). Purity was 98% and the purity reduced yield for 3-ethoxyphthalimide was 77.

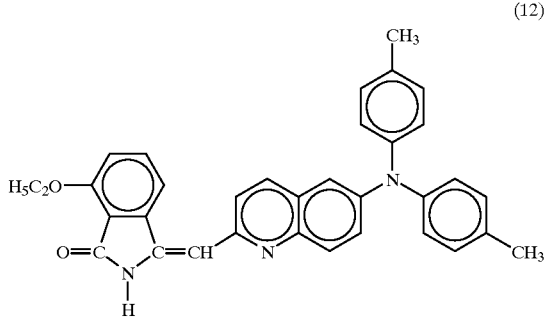

(12)

Result of MS spectrum was as follows. m/e=487
Following results were obtained by elemental analysis.

|  | C | H | N |
|---|---|---|---|
| Calculated (%) | 78.5 | 6.0 | 8.6 |
| Found (%) | 58.9 | 2.5 | 5.7 |

(EL Element Preparation Example-8)

On an ITO glass substrate, N,N,N',N'-tetra(4-ditolylaminophenyl)-1,4-phenylenediamine was stacked to a film thickness of 50 nm under vacuum of 5×10⁻⁶ torr by a resistance heating method. Successively, the quinoline compound of the formula (12) was stacked to a film thickness of 50 nm and further, an aluminum electrode was deposited to a film thickness of 150 nm under vacuum of 6×10⁻⁵ torr. A positive electric field was applied to the ITO side of the element and a negative electric field was applied to the aluminum side. The emission from the surface of ITO glass substrate of the element was observed. When a voltage of 19V was applied, the emission was stable and the emission of 118 Cd/m² was obtained.

(Fluorescent Material Preparation Example-8)

The quinoline compound of the formula (12) was added to polyethylene terephthalate resin powder, hot pressed at 280° C. and cooled to obtain a sheet having thickness of 0.5 mm. The sheet was measured with a fluorophotometer: FP-770, manufactured by Nippon Bunko Co. Emission at 530 nm and excitation at 380 nm were obtained.

EXAMPLES 9–15

Experimental Examples for Process A

The same reaction procedures as described in Example 1 were carried out by using phthalimide base compounds or quinaldine base compounds as shown in Table 1. The purity reduced yields of quinoline derivatives obtained are illustrated in Table 1.

| | phthalimide base compounds | quinaldine base compounds | purity reduced yield |
|---|---|---|---|
| 9 | 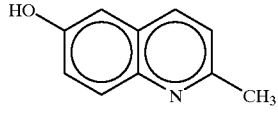 | 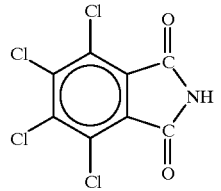 | 70 |
| 10 | 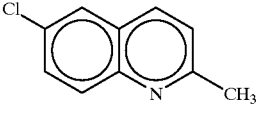 | 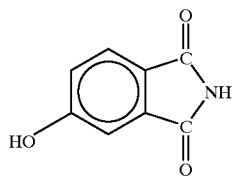 | 65 |
| 11 | 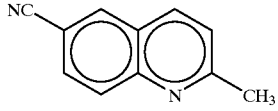 | 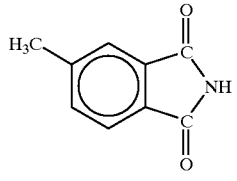 | 75 |
| 12 | 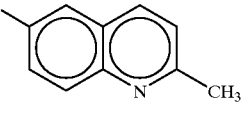 | 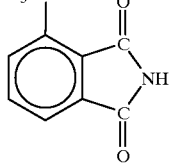 | 75 |
| 13 | 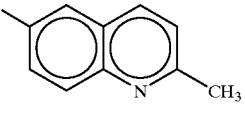 | 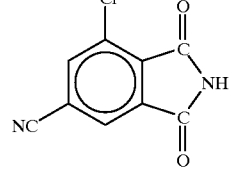 | 70 |
| 14 | 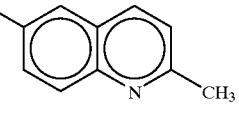 | 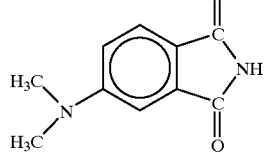 | 70 |
| 15 | 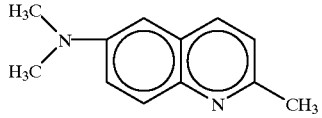 | 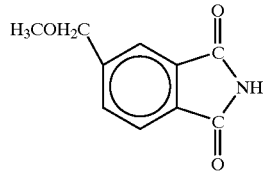 | 75 |

EXAMPLE 16

Preparation Example-16

Experimental Example for Process D

To a reaction vessel, 143 g (1.00 mole) of quinaldine, 78 g (0.531 mol) of phthalimide, 136.3 g (1.00 mole) of zinc chloride and 2000 g of N,N-dimethylaniline were charged and heated under nitrogen ventilation at 180° C. for 15 hours. After cooling to room temperature, the solid portion was filtered, washed with 4000 g of methanol, sludged with 3000 g of DMF, filtered, washed with methanol, and dried to obtain 120 g of the quinoline compound having the formula (13). Purity was 97% and the purity reduced yield was 65% for phthalimide.

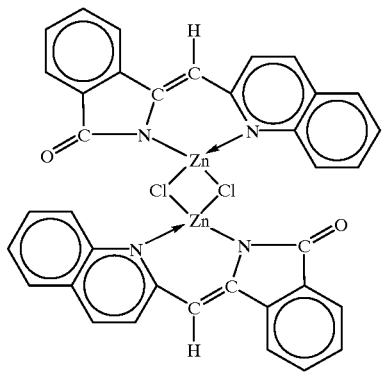

(13)

Figure 5:
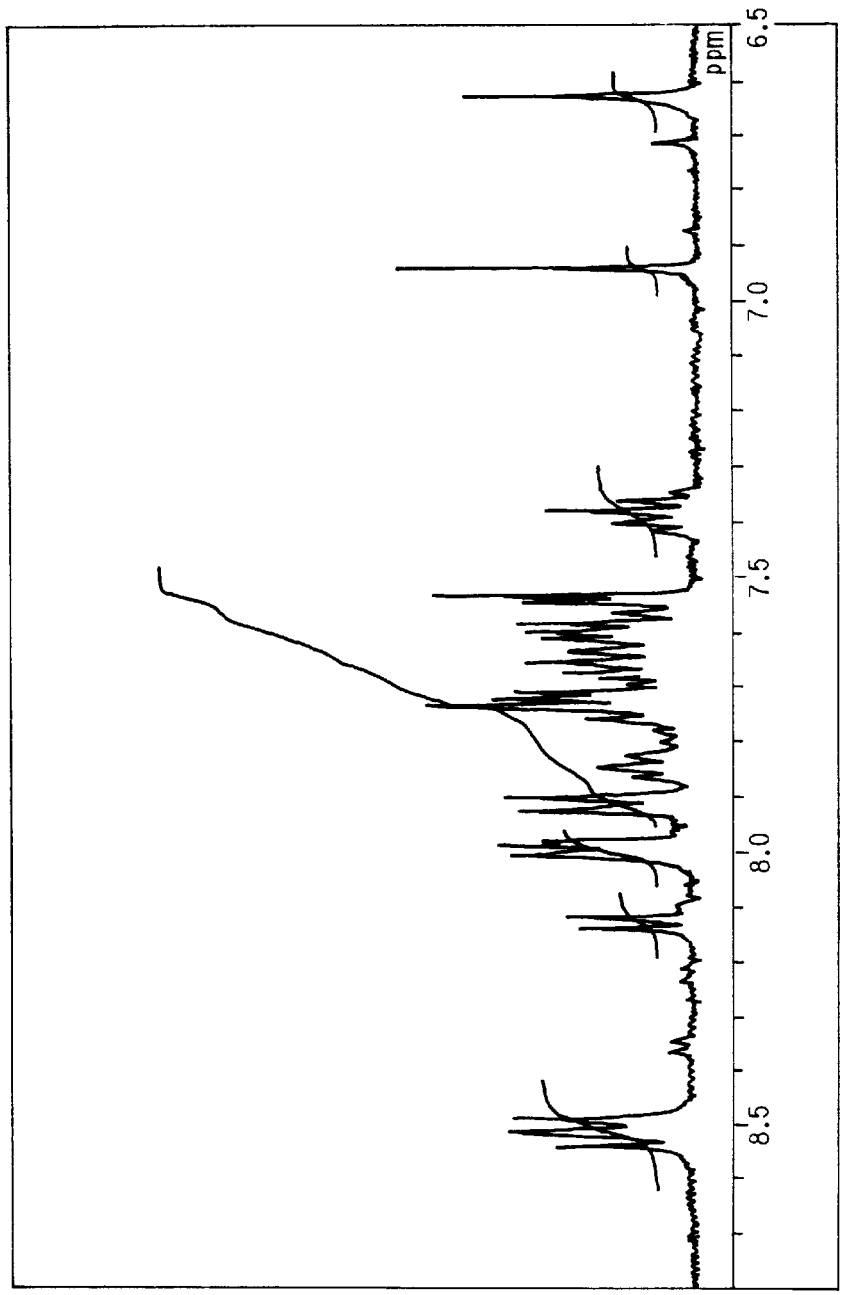
FIG. 5 is a NMR chart of a zinc chloride complex obtained in Example 16 and shown by the formula (13).

NMR chart of the compound (13) was illustrated in FIG. 5.

Following results were obtained by elemental analysis.

|  | C | H | N | Zn | Cl |
|---|---|---|---|---|---|
| Calculated (%) | 58.1 | 3.0 | 7.5 | 17.6 | 9.6 |
| Found (%) | 57.3 | 3.0 | 7.6 | 17.4 | 9.6 |

(EL Element Preparation Example-16)

On an ITO glass substrate, N,N'-diphenyl-N,N'-ditolyl-1,1'-diphenyl-4,4'-diamine was stacked to a film thickness of 50 nm under vacuum of $5 \times 10^{-5}$ torr by a resistance heating method. Successively, the quinoline compound of the formula (13) was stacked to a film thickness of 50 nm and further, an aluminum electrode was deposited to a film thickness of 150 nm under vacuum of $6 \times 10^{-5}$ torr. A positive electric field was applied to the ITO side of the element and a negative electric field was applied to the aluminum side. The emission from the surface of ITO glass substrate of the element was observed. As a voltage of 19V and a current density of 26 mA/cm$^2$, the emission was stable and the emission of 115 Cd/m$^2$ was obtained.

(Ultraviolet Absorbing Material Preparation Example-16)

The compound of the formula (13) was added to polyethylene terephthalate resin powder, hot pressed at 280° C., and cooled to obtain a sheet having thickness of 0.5 nm. The sheet was measured with a spectrophotometer: UV-3100PC, manufactured by Shimadzu Seisakusho Co. Ultraviolet transmittance at 380 nm was 2%.

EXAMPLE 17

Preparation Example-17

Experimental Example for Process D

To a reaction vessel, 219 g (1.00 mole) of 5-phenylquinaldine, 142.5 g (0.5 mol) of 3,4,5,6-tetrachlorophthalimide, 136.g (0.604 mole) of zinc bromide and 2000 g of N,N-dimethylaniline were charged and heated under nitrogen ventilation at 180° C. for 15 hours. After cooling to room temperature, the solid portion was filtered, washed with 4000 g of methanol, sludged with 3000 g of DMF, filtered, washed with methanol, and dried to obtain 200 g of the quinoline compound having the formula (14).

Purity was 97% and the purity reduced yield was 65% for 3,4,5,6-tetrachlorophthalimide.

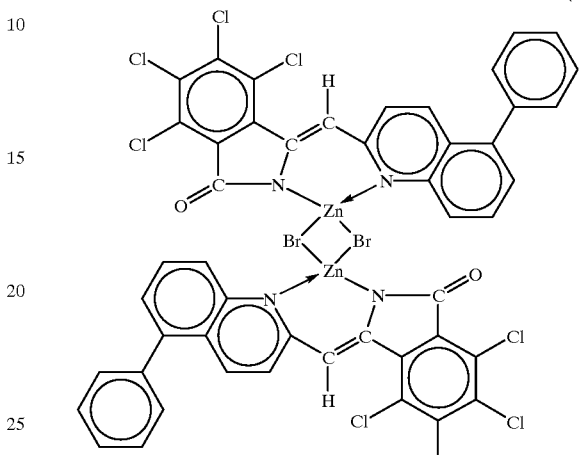

(14)

Following results were obtained by elemental analysis.

|  | C | H | N | Zn |
|---|---|---|---|---|
| Calculated (%) | 45.7 | 1.8 | 4.4 | 10.4 |
| Found (%) | 45.2 | 1.9 | 5.1 | 10.4 |

(EL Element Preparation Example-17)

On a glass substrate which formed an ITO transparent electrode, 1,1-bis(4-N,N-ditolylaminophenyl)cyclohexanone was stacked to a film thickness of 50 nm. Successively, the quinoline compound of the formula (13) was stacked to a film thickness of 50 nm, and further 2,2',6,6'-tetramethyldiphenoquinone was stacked to a film thickness of 50 nm. A back electrode was formed by stacking indium to a film thickness of 150 nm. When a voltage of 8V was applied, emission of 300 Cd/m$^2$ was obtained.

(Ultraviolet Absorbing Material Preparation Example-17)

The compound of the formula (14) was added to polyethylene terephthalate resin powder, hot pressed at 280° C., and cooled to obtain a sheet having thickness of 0.5 nm. The sheet was measured with a spectrophotometer: UV-3100PC, manufactured by Shimadzu Seisakusho Co. Ultraviolet transmittance at 380 nm was 4%.

EXAMPLE 18

Preparation Example-18

Experimental Example for Process D

To a reaction vessel, 338 g (1.00 mole) of 6-N,N-ditolylamino-2-quinaldine, 95 g (0.5 mol) of 3-ethoxyphthalimide, 136.3 g (1.00 mole) of zinc chloride, 6000 g of o-dichlorobenzene and 200 g of isoquinoline were charged and heated under nitrogen ventilation at 180° C. for 45 hours. After cooling to room temperature, the solid portion was filtered, washed with 5000 g of methanol, sludged with 4000 g of methanol, filtered, washed with methanol, and dried to obtain 160 g of the compound having the formula (15). Purity was 98% and the purity reduced yield was 54%.

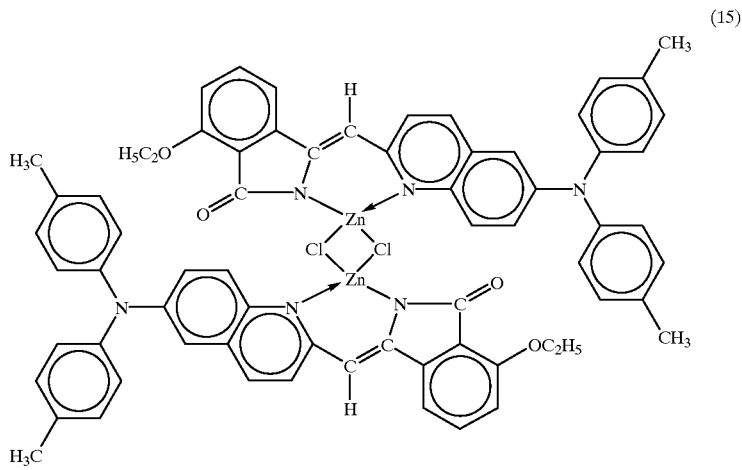

(15)

Following results were obtained by elemental analysis.

|  | C | H | N | Zn | Cl |
|---|---|---|---|---|---|
| Calculated (%) | 65.4 | 4.8 | 7.2 | 11.1 | 6.0 |
| Found (%) | 65.2 | 5.0 | 7.7 | 11.1 | 6.1 |

(EL Element Preparation Example-18)

On an ITO glass substrate, N,N,N',N'-tetra(4-ditrylaminophenyl)-1,4-phenylenediamine was stacked to a film thickness of 50 nm under vacuum of $5 \times 10^{-6}$ torr by a resistance heating method. Successively, the compound of the formula (15) was stacked to a film thickness of 50 nm and further, an aluminum electrode was deposited to a film thickness of 150 nm under vacuum of $6 \times 10^{-5}$ torr. A positive electric field was applied to the ITC side of the element and a negative electric field was applied to the aluminum side. The emission from the surface of ITO glass substrate of the element was observed. As a voltage of 9 V, the emission was stable and the emission of 120 Cd/m² was obtained.

(Ultraviolet Absorbing Material Preparation Example-18)

The compound of the formula (15) was added to polyethylene terephthalate resin powder, hot pressed at 280° C., and cooled to obtain a sheet having thickness of 0.5 mm. The sheet was measured with a spectrophotometer: UV-3100PC, manufactured by Shimadzu Seisakusho Co. Ultraviolet transmittance at 370 nm was 3%.

EXAMPLE 19

Preparation Example-19

Experimental Example for Process F

To 200 g of pyridine, 20 g of the compound having the formula (13) was added and heated with stirring at 110–115° C. for 8 hours. After cooling the reaction mixture, the precipitated solid was filtered, throughly washed with water, and dried to obtain 14.9 g of the compound having the formula (16).

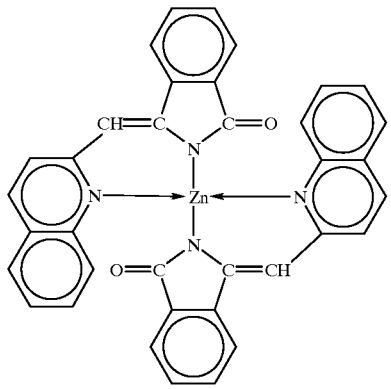

(16)

Figure 6:
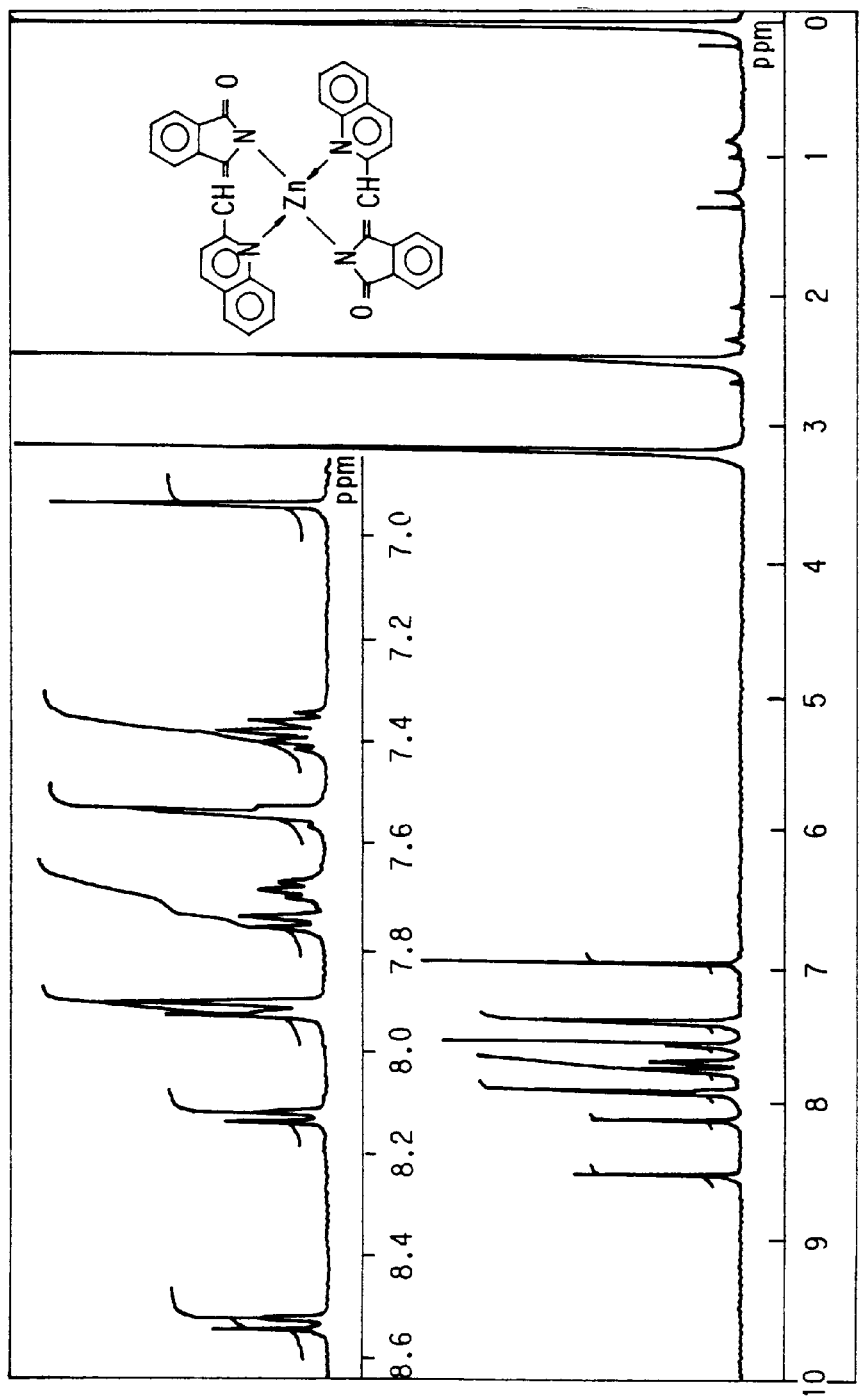
FIG. 6 is a NMR chart of a zinc complex obtained in Example 19 and shown by the formula (16).
Figure 7:
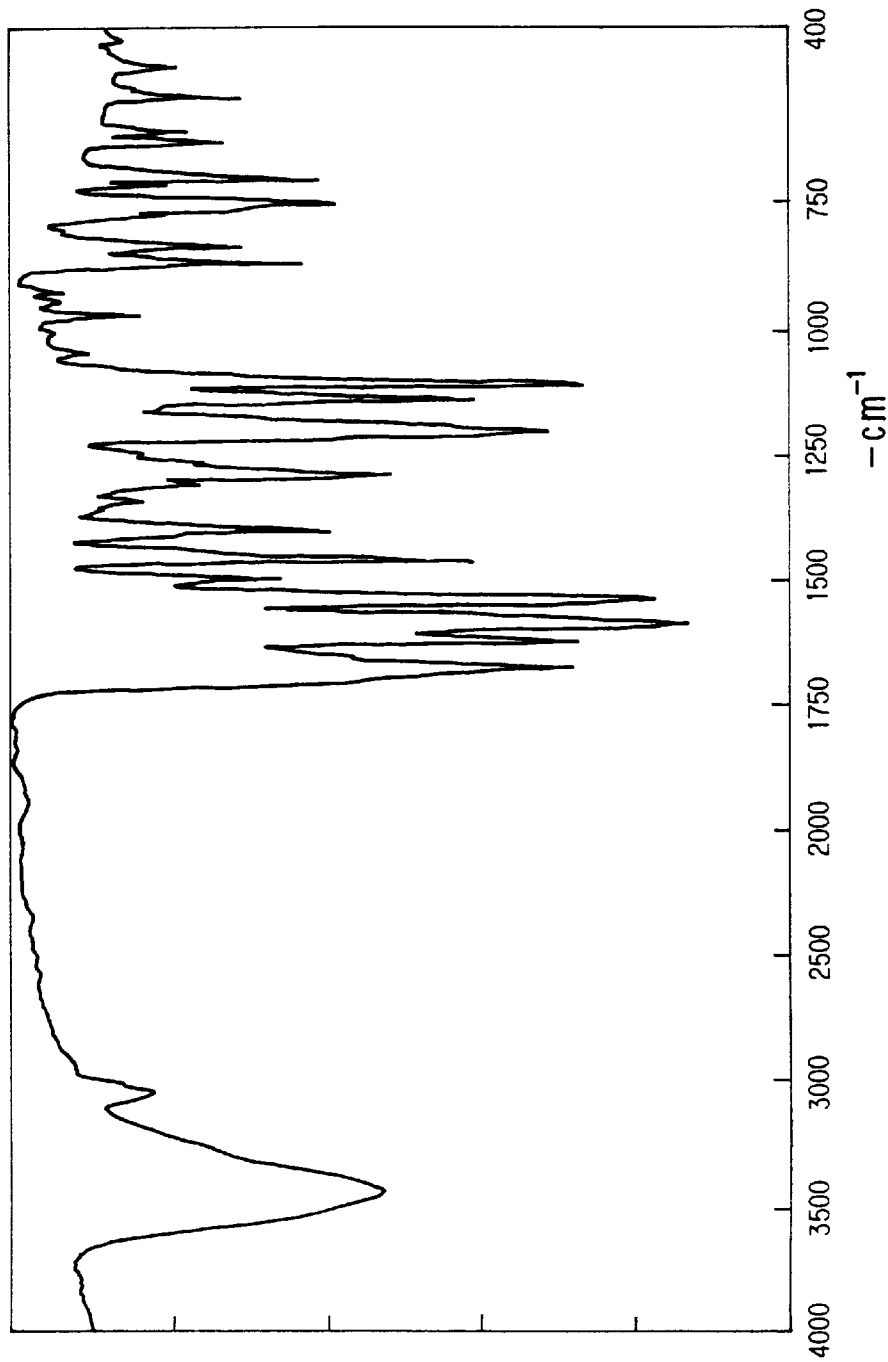
FIG. 7 is IR spectrum of a zinc complex obtained in Example 19 and shown by the formula (16).
Figure 8:
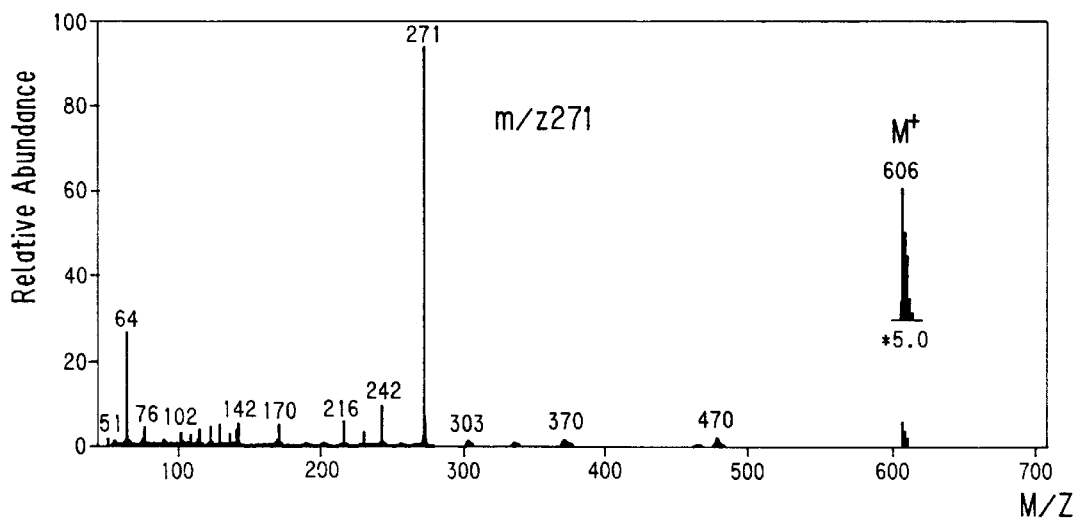
FIG. 8 is a MS spectrum of a zinc complex obtained in Example 19 and shown by the formula (16).
Figure 8:
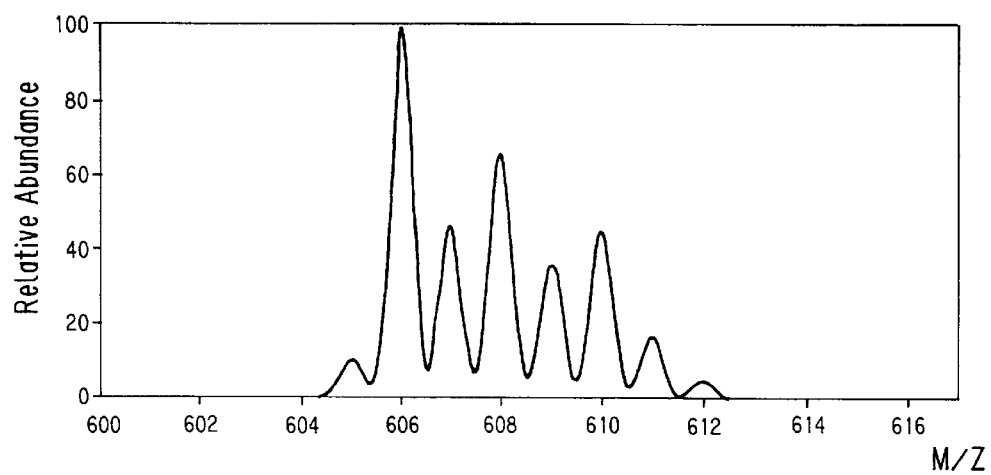

FIG. 6 illustrates an NMR chart, FIG. 7 illustrates an IR spectrum, and FIG. 8 illustrates an MS spectrum of the compound having the formula (16), respectively.

Following results were obtained by elemental analysis.

|  | C | H | N | Zn |
|---|---|---|---|---|
| Calculated | 71.2 | 3.6 | 9.2 | 10.7 |
| Found | 69.6 | 3.7 | 9.0 | 10.6 |

(EL Element Preparation Example-19)

On an ITO glass substrate, N,N'-diphenyl-N,N'-ditolyl-1,1'-diphenyl-4,4'-diamine was stacked to a film thickness of 50 nm under vacuum of $5 \times 10^{-5}$ torr by a resistance heating method. Successively, the compound of the formula (16) was stacked to a film thickness of 50 nm and further, an aluminum electrode was deposited to a film thickness of 150 nm under vacuum of $6 \times 10^{-5}$ torr. A positive electric field was applied to the ITO side of the element and a negative electric field was applied to the aluminum side. The emission from the surface of ITO glass substrate of the element was observed. As a voltage of 19 V and a current density of 26 mA/cm², the emission was stable and the emission of 115 Cd/m² was obtained.

(Ultraviolet Absorbing Material Preparation Example-19)

The compound of the formula (16) was added to polyethylene terephthalate resin powder, hot pressed at 280° C., and cooled to obtain a sheet having thickness of 0.5 mm. The sheet was measured with a spectrophotometer: UV-3100PC, manufactured by Shimadzu Seisakusho Co. Ultraviolet transmittance at 380 nm was 5%.

EXAMPLE 20

Preparation Example 20

Experimental Example for Process F

To 200 g of γ-picoline pyridine, 20 g(0.0167 mole) of the compound having the formula (14) was added and heated with stirring at 110–115° C. for 8 hours. After cooling the reaction mixture, the precipitated solid was filtered, throughly washed with water, and dried to obtain 13.5 g of the compound having the formula (17).

(EL Element Preparation Example-20)

On a glass substrate which formed an ITO transparent electrode, 1,1-bis(4-N,N-ditolylaminophenyl) cyclohexanone was stacked to a film thickness of 50 nm. Successively, the quinoline compound of the formula (17) was stacked to a film thickness of 50 nm, and further 2,2',6,6'-tetramethyldiphenoquinone was stacked to a film thickness of 50 nm. A back electrode was formed by stacking indium to a film thickness of 150 nm. When a voltage of 8 V was applied, emission of 300 Cd/m$^2$ was obtained.

(Ultraviolet Absorbing Material Preparation Example-20)

The compound of the formula (17) was added to polyethylene terephthalate resin powder, hot pressed at 280° C., and cooled to obtain a sheet having thickness of 0.5 mm. The sheet was measured with a spectrophotometer: UV-3100PC, manufactured by Shimadzu Seisakusho Co. Ultraviolet transmittance at 380 nm was 4%.

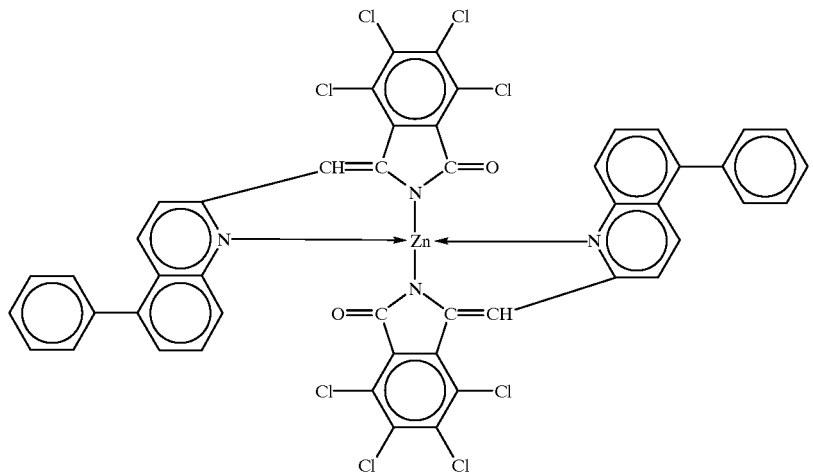

(17)

Result of MS spectrum was as follows. m/e=1035

Following results were obtained by elemental analysis.

|  | C | H | N | Zn | Cl |
|---|---|---|---|---|---|
| Calculated (%) | 55.7 | 2.1 | 5.4 | 27.4 | 6.3 |
| Found (%) | 55.1 | 2.0 | 5.5 | 27.3 | 6.3 |

EXAMPLE 21

Preparation Example 21

Experimental Example for Process F

To 200 g of γ-picoline pyridine, 20 g(0.0173 mole) of the compound having the formula (15) was added and heated with stirring at 110–115° C. for 8 hours. After cooling the reaction mixture, the precipitated solid was filtered, throughly washed with water, and dried to obtain 13.5 g of the compound having the formula (18).

(18)

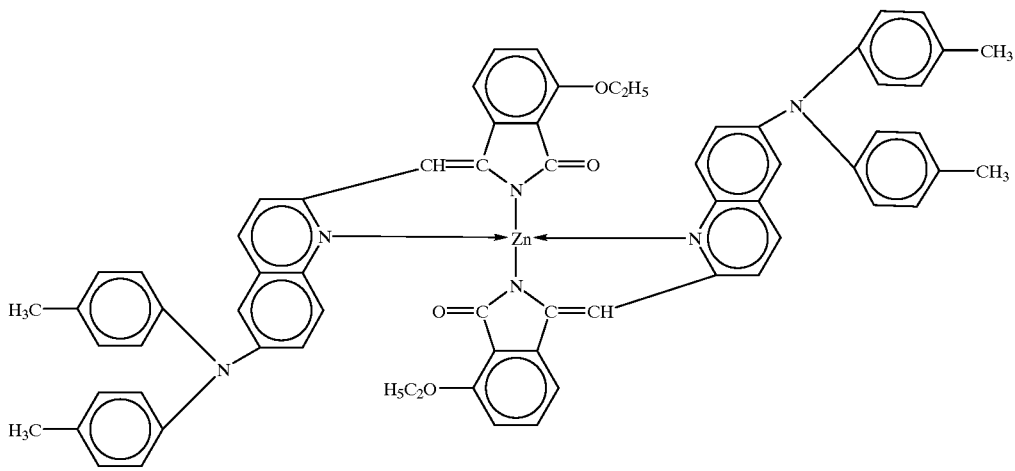

Result of MS spectrum was as follows. m/e=1038
Following results were obtained by elemental analysis.

|  | C | H | N | Zn |
|---|---|---|---|---|
| Calculated (%) | 74.0 | 5.4 | 8.1 | 6.3 |
| Found (%) | 74.0 | 6.5 | 8.1 | 6.2 |

(EL Element Preparation Example-21)

On an ITO glass substrate, N,N,N',N'-tetra(4-ditolylaminophenyl)-1,4-phenylenediamine was stacked to a film thickness of 50 nm under vacuum of $5\times10^{-6}$ torr by a resistance heating method. Successively, the compound of the formula (18) was stacked to a film thickness of 50 nm and further, an aluminum electrode was deposited to a film thickness of 150 nm under vacuum of $6\times10^{-5}$ torr. A positive electric field was applied to the ITC side of the element and a negative electric field was applied to the aluminum side. The emission from the surface of ITO glass substrate of the element was observed. As a voltage of 9 V, the emission was stable and the emission of 120 Cd/m$^2$ was obtained.

(Ultraviolet Absorbing Material Preparation Example-21)

The compound of the formula (18) was added to polyethylene terephthalate resin powder, hot pressed at 280° C., and cooled to obtain a sheet having thickness of 0.5 mm. The sheet was measured with a spectrophotometer: UV-3100PC, manufactured by Shimadzu Seisakusho Co. Ultraviolet transmittance at 375 nm was 2%.

EXAMPLE 22

Experimental Example for Process B

To 1000 g of a 10% aqueous hydrochloric acid solution, 25 g(0.0369 mole) of the compound having the formula (13) was added and heated with stirring at 95° C. for an hour. Solid reaction mass was isolated, washed with water and dried to obtain 17 g of the compound having the formula (7). Purity was 99%.

EXAMPLE 23

Experimental Example for Process B

To 1000 g of a 10% aqueous hydrochloric acid solution, 25 g(0.0209 mole) of the compound having the formula (14) was added and heated with stirring at 95° C. for an hour. Solid reaction mass was isolated, washed with water and dried to obtain 16 g of the compound having the formula (11). Purity was 98%.

EXAMPLE 24

Experimental Example for Process B

To 800 g of a 10% aqueous hydrochloric acid solution, 25 g(0.0216 mole) of the compound having the formula (15) was added and heated with stirring at 95° C. for an hour. Solid reaction mass was isolated, washed with water and dried to obtain 18 g of the compound having the formula (12). Purity was 97%.

EXAMPLE 25

Experimental Example for Process C

To 1200 g of a 10% aqueous hydrochloric acid solution, 35 g(0.0576 mole) of the compound having the formula (16) was added and heated with stirring at 95° C. for an hour. Solid reaction mass was isolated, washed with water and dried to obtain 29 g of the compound having the formula (7). Purity was 100%.

EXAMPLE 26

Experimental Example for Process C

To 1320 g of a 10% aqueous hydrochloric acid solution, 35 g(0.0338 mole) of the compound having the formula (17) was added and heated with stirring at 95° C. for an hour. Solid reaction mass was isolated, washed with water and dried to obtain 31 g of the compound having the formula (11). Purity was 99%.

EXAMPLE 27

Experimental Example for Process C

To 960 g of a 10% aqueous hydrochloric acid solution, 35 g(0.0322 mole) of the compound having the formula (18) was added and heated with stirring at 95° C. for an hour. Solid reaction mass was isolated, washed with water and dried to obtain 32 g of the compound having the formula (12). Purity was 99%.

EXAMPLE 28

Experimental Example for Process E

To 200 g of N,N-dimethylaniline, 20 g(0.0735 mole) of the compound having the formula (7) and 25.2 g (0.185 mole) of zinc chloride were added and heated with stirring at 180° C. for 7 hours. After cooling, the reaction mixture was poured into 800 ml of methanol and stirred at room temperature for an hour. The precipitated solid was filtered, washed with water and dried to obtain 15.5 g of the compound having the formula (13). Purity was 98%.

EXAMPLE 29

Experimental Example for Process E

To 200 g of N,N-dimethylaniline, 20 g(0.0391 mole) of the compound having the formula (12) and 5.6 g (0.041 mole) of zinc chloride were added and heated with stirring at 150° C. for 27 hours. After cooling, the reaction mixture was poured into 800 ml of methanol and stirred at room temperature for an hour. The precipitated solid was filtered, washed with water and dried to obtain 28.9 g of the compound having the formula (15). Purity was 98%.

EXAMPLE 30

Experimental Example for Process G

To a reaction vessel, 50 g (0.34 mole) of phthalimide, 97.3 g (0.68 mole) of quinaldine, 99 g (0.73 mole) of zinc chloride, and 400 g of N,N-dimethylaniline were charged and heated under nitrogen ventilation at 180° C. for 10 hours. The reaction mixture was poured into 1720 g of pyridine and treated at 110° C. for 9 hours. After cooling to room temperature, the precipitate was filtered, washed with water, and dried to obtain 95 g of the compound having the formula (16). Purity was 99%.

EXAMPLE 31

Experimental Example for Process G

To a reaction vessel, 219 g (1.0 mole) of 5-phenylquinaldine, 143 g (0.5 mole) of 3,4,5,6-tetrachlorophthalimide, 136 g (0.604 mole) of zinc bromide, and 2000 g of N,N-dimethylaniline were charged and heated under nitrogen ventilation at 180° C. for 15 hours. The reaction mixture was poured into 100 g of γ-picoline and treated at 110° C. for 6 hours. After cooling to room temperature, the precipitate was filtered, washed with water, and dried to obtain 298 g of the compound having the formula (17). Purity was 99%.

COMPARATIVE EXAMPLE 1

An EL element was prepared by stacking the compound having the formula below in place of the compound (7) in Example 1. The EL element had an emission intensity of 80 Cd/m².

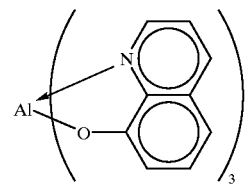

What is claimed is:

1. A zinc halogenide complex and a tautomer of the same which are represented by the formula (2):

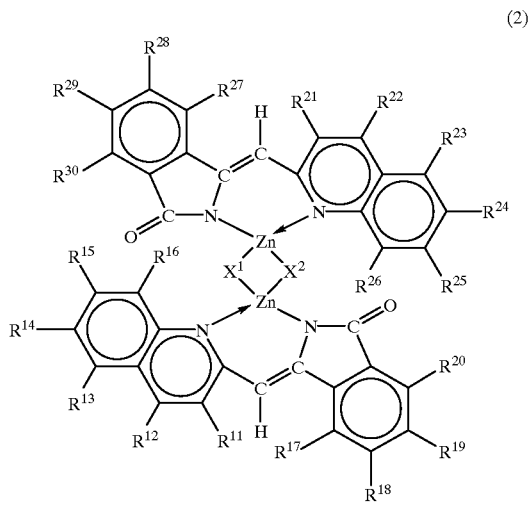

wherein each of $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$ and $R^{30}$ is individually a hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, and each of $X^1$ and $X^2$ is individually a fluorine, chlorine, bromine or iodine atom.

2. A preparation process of a zinc halogenide complex represented by the formula (2) and a tautomer of the same according to claim 1, comprising reacting one or two quinoline derivatives represented by the formula (5):

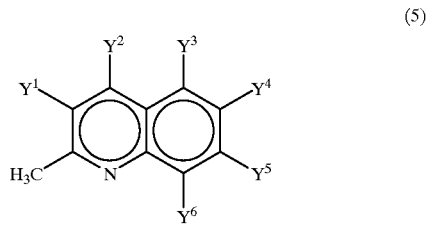

wherein each of $Y^1$, $Y^2$, $Y^3$, $Y^4$, $Y^5$ and $Y^6$ is a hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N- dialkylamino, substituted or unsubstituted N-arylamino, substituted or unsubstituted N,N-diarylamino or substituted or unsubstituted N-alkyl-N-arylamino group, and 0.2 to 10 moles of one or two phthalimide derivatives represented by the formula (6):

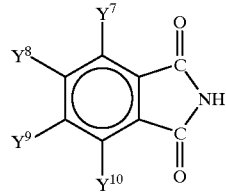

(6)

wherein each of $Y^7$, $Y^8$, $Y^9$ and $Y^{10}$ is individually a hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, per mole of the quinoline derivatives of the formula (5), with 0.1 to 50 moles of a zinc halogenide selected from the group consisting of zinc fluoride, zinc chloride, zinc bromide and zinc iodide per mole of the quinoline derivative of the formula (5) in 1 to 50 parts by weight of an organic basic solvent per part by weight of the quinoline derivative of the formula (5).

3. A preparation process of a zinc halogenide complex represented by the formula (2) and a tautomer of the same according to claim 1, comprising reacting a quinoline compound represented by the formula (4)

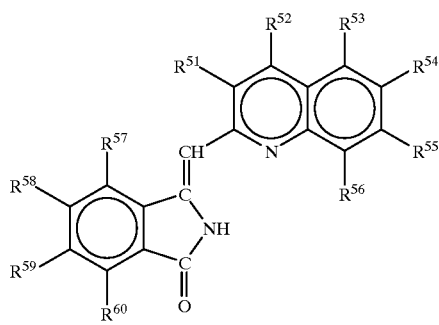

(4)

wherein each of $R^{51}$, $R^{52}$, $R^{53}$, $R^{54}$, $R^{55}$, $R^{56}$, $R^{57}$, $R^{58}$, $R^{59}$ and $R^{60}$ is individually a hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, with 0.1 to 50 moles of a zinc halogenide selected from the group consisting of zinc fluoride, zinc chloride, zinc bromide and zinc iodide per mole of the quinoline derivative of the formula (4) in 1 to 50 parts by weight of an organic basic solvent per part by weight of the quinoline derivative of the formula (4).

4. An electro-luminescence element comprising a luminous layer consisting of a zinc halogenide complex represented by the formula (2) and a tautomer of the same according to claim 1.

5. An ultraviolet absorption material comprising a zinc halogenide complex represented by the formula (2) and a tautomer of the same according to claim 1.

6. A zinc complex and tautomer of the same which are represented by the formula (3):

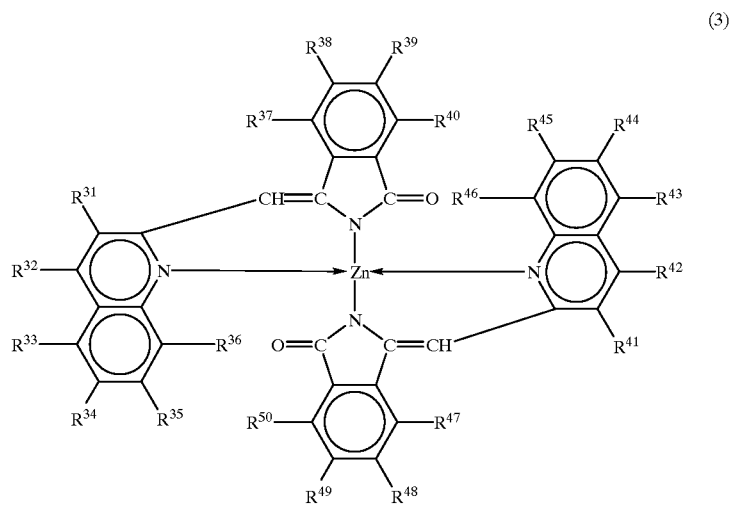

(3)

wherein each of $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$ and $R^{50}$ is individually hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group.

7. A preparation process of a zinc complex represented by the formula (3) and a tautomer of the same according to claim 3 comprising heating in 6 to 100 parts by weight of organic amine, one part by weight of a zinc halogenide complex represented by the formula (2) and a tautomer of the same;

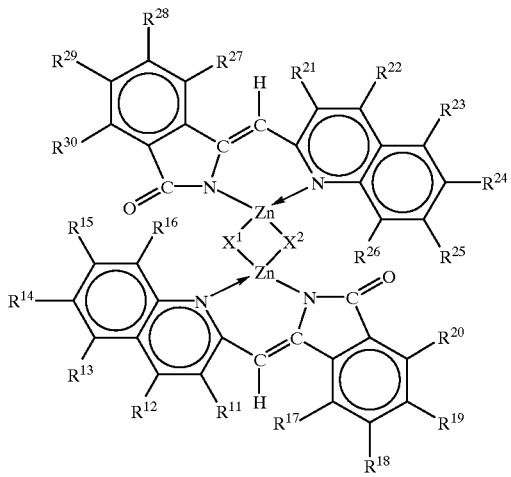

(2)

wherein each of $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$ and $R^{30}$ is individually a hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, and each of $X^1$ and $X^2$ is individually a fluorine, chlorine, bromine or iodine atom.

8. A preparation process of a zinc complex represented by the formula (3) and a tautomer of the same according to claim 6 comprising reacting one or two quinoline derivatives represented by the formula (5)

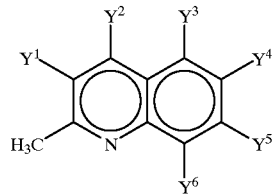

(5)

wherein each of $Y^1$, $Y^2$, $Y^3$, $Y^4$, $Y^5$ and $Y^6$ is a hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, and 0.2 to 10 moles of one or two phthalimide derivatives represented by the formula (6):

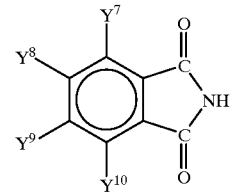

(6)

wherein each of $Y^7$, $Y^8$, $Y^9$ and $Y^{10}$ is individually a hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, per mole of the quinoline derivative of the formula (5), with 0.1 to 50 moles of a zinc halogenide selected from the group consisting of zinc fluoride, zinc chloride, zinc bromide and zinc iodide per mole of the quinoline derivative of the formula (5) in 1 to 50 parts by weight of an organic basic solvent per part by weight of the quinoline derivative of the formula (5).

9. An electro-luminescence element comprising a luminous layer consisting of a zinc complex represented by the formula (3) and a tautomer of the same according to claim 6.

10. An ultraviolet absorption material comprising a zinc complex represented by the formula (3) and a tautomer of the same according to claim 6.

11. A quinoline compound which has peak intensity at a Bragg angle (2 θ) of 12.8°, 15.2°, 18.3°, 22.5°, 25° and 28.4° and no peak intensity at 13.9° on a X-ray diffraction spectrum and is shown by the formula (7):

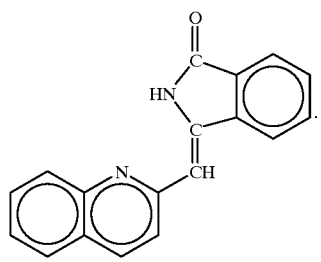

(7)

12. A quinoline compound of the formula (7) wherein the peak intensity ratio of the Bragg angle (2 θ) of 12.8° to the Bragg angle (2 θ) of 15.2° is 0.7 or less, said quinoline compound having no peak intensity at a Bragg angle (2 θ) of 13.9° and wherein formula (7) is as follows;

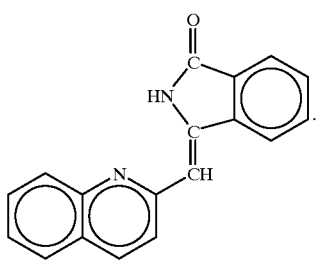

13. A fluorescent material comprising a quinoline compound which has peak intensity at a Bragg angle (2 θ) of 12.8°, 15.2°, 18.3°, 22.5°, 25° and 28.4° and no peak intensity at 13.9° on a X-ray diffraction spectrum and is shown by the formula (7) as follows:

(7)

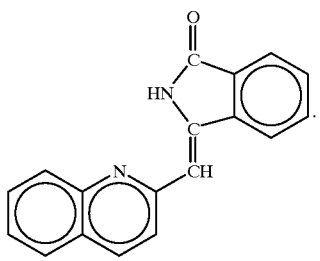

14. A fluorescent material comprising a quinoline compound represented by the formula (7) wherein the peak intensity ratio of the Bragg angle (2 θ) of 12.8° to the Bragg angle (2 θ) of 15.2° is 0.7 or less, said quinoline compound having no peak intensity at a Bragg angle (2 θ) of 13.9° and wherein formula (7) is as follows:

(7)

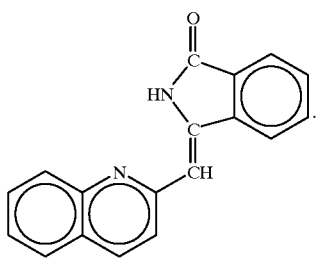

15. A preparation process of a quinoline compound and a tautomer of the same which are represented by the formula (4):

(4)

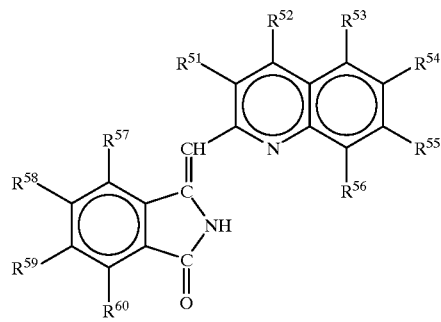

wherein each of $R^{51}$, $R^{52}$, $R^{53}$, $R^{54}$, $R^{55}$, $R^{56}$, $R^{57}$, $R^{58}$, $R^{59}$ and $R^{60}$ is individually a halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, comprising treating a zinc halogenide complex and a tautomer of the same which are represented by the formula (2) with 2 to 200 moles of an inorganic acid per mole of the complex/tautomer of the formula (2)

(2)

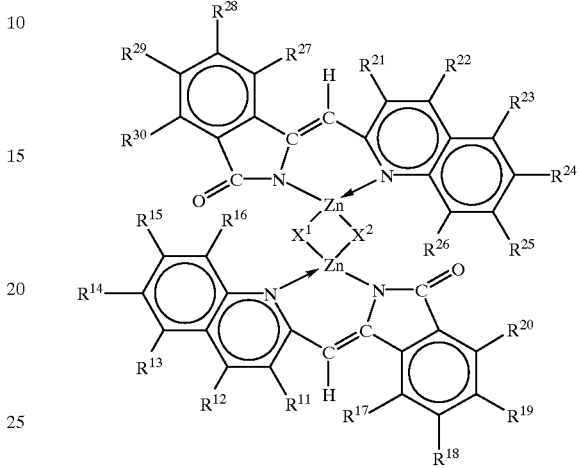

wherein each of $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$ and $R^{30}$ is individually a hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, and each of $X^1$ and $X^2$ is individually a fluorine, chlorine, bromine or iodine atom.

16. A preparation process of a quinoline compound and a tautomer of the same which are represented by the formula (4):

(4)

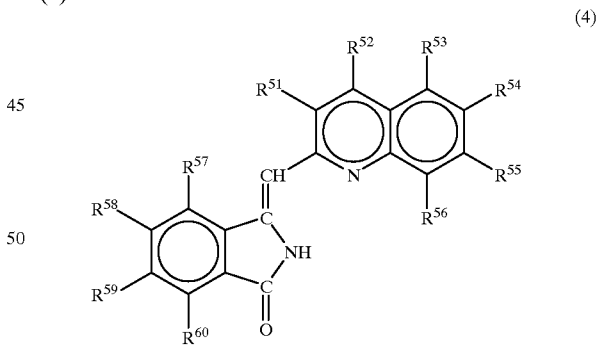

wherein each of $R^{51}$, $R^{52}$, $R^{53}$, $R^{54}$, $R^{55}$, $R^{56}$, $R^{57}$, $R^{58}$, $R^{59}$ and $R^{60}$ is individually halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group, comprising treating a zinc complex and a tautomer of the same which are represented by the formula (3) with 2 to 200 moles of an inorganic acid per mole of the complex/tautomer of the formula (3)

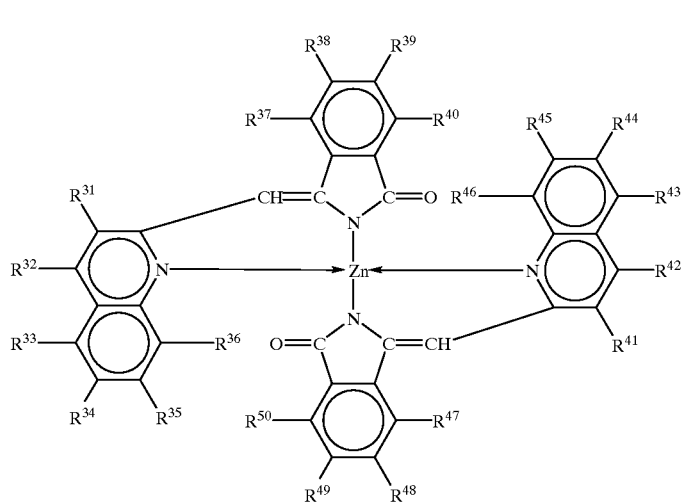

(3)

wherein each of $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$ and $R^{50}$ is individually hydrogen atom, halogen atom, nitro, cyano, hydroxy, amino, substituted or unsubstituted alkyl, substituted or unsubstituted aryl, substituted or unsubstituted alkoxy, substituted or unsubstituted aryloxy, substituted or unsubstituted N-alkylamino, substituted or unsubstituted N,N-dialkylamino, substituted or unsubstituted N-arylamino, substituted or unsubstituted N,N-diarylamino or substituted or unsubstituted N-alkyl-N-arylamino group.

* * * * *